(12) United States Patent
Weigel et al.

(10) Patent No.: US 11,745,168 B2
(45) Date of Patent: Sep. 5, 2023

(54) BIFUNCTIONAL METAL OXIDES AND PARAFFIN ISOMERIZATION THEREWITH

(71) Applicant: ExxonMobil Technology and Engineering Company, Annandale, NJ (US)

(72) Inventors: Scott J. Weigel, Allentown, PA (US); Megan E. Witzke, Bedminster, NJ (US); Wesley Sattler, Parsippany, NJ (US); Brandon M. Carcuffe, Hackettstown, NJ (US); Jihad M. Dakka, Whitehouse Station, NJ (US); Ryan S. Dugan, Milford, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 120 days.

(21) Appl. No.: 17/349,986

(22) Filed: Jun. 17, 2021

(65) Prior Publication Data
US 2022/0401922 A1    Dec. 22, 2022

(51) Int. Cl.
*B01J 23/00* (2006.01)
*B01J 6/00* (2006.01)
(Continued)

(52) U.S. Cl.
CPC ............. *B01J 23/002* (2013.01); *B01J 6/001* (2013.01); *B01J 21/066* (2013.01); *B01J 23/888* (2013.01);
(Continued)

(58) Field of Classification Search
CPC ........ B01J 23/002; B01J 6/001; B01J 21/066; B01J 23/888; B01J 35/0026;
(Continued)

(56) References Cited

U.S. PATENT DOCUMENTS

| 5,510,309 A | 4/1996 | Chang et al. |
| 5,993,643 A | 11/1999 | Chang et al. |

(Continued)

FOREIGN PATENT DOCUMENTS

| CN | 1394677 A | * | 2/2003 | ............. B01J 21/06 |
| CN | 106140197 A | * | 11/2016 | ............ B01J 27/053 |
| WO | WO1996/013328 | | 5/1996 | |

OTHER PUBLICATIONS

U.S. Appl. No. 17/807,024, filed Jun. 15, 2022, Sattler, W. et al.
(Continued)

*Primary Examiner* — Patricia L. Hailey

(57) ABSTRACT

Tungstated zirconium catalysts for paraffin isomerization may comprise: a mixed metal oxide that is at least partially crystalline and comprises tungsten, zirconium, and a variable oxidation state metal selected from Fe, Mn, Co, Cu, Ce, Ni, and any combination thereof. The mixed metal oxide comprises about 5 wt. % to about 25 wt. % tungsten, about 40 wt. % to about 70 wt. % zirconium, and about 0.01 wt. % to about 5 wt. % variable oxidation state metal, each based on a total mass of the mixed metal oxide. The mixed metal oxide has a total surface area of about 50 $m^2/g$ or greater as measured according to ISO 9277, and at least one of the following: an ammonia uptake of about 0.05 to about 0.3 mmol/g as measured by temperature programmed adsorption/desorption, or a collidine uptake of about 100 µmol/g or greater as measured gravimetrically.

31 Claims, 5 Drawing Sheets

(51) Int. Cl.
- B01J 21/06 (2006.01)
- B01J 23/888 (2006.01)
- B01J 35/00 (2006.01)
- B01J 35/10 (2006.01)
- B01J 37/03 (2006.01)
- C07C 5/27 (2006.01)
- B01J 37/00 (2006.01)

(52) U.S. Cl.
CPC ....... B01J 35/0026 (2013.01); B01J 35/1014 (2013.01); B01J 35/1019 (2013.01); B01J 37/03 (2013.01); C07C 5/2705 (2013.01); B01J 37/0009 (2013.01); C07C 2521/06 (2013.01); C07C 2523/888 (2013.01)

(58) Field of Classification Search
CPC .... B01J 35/1014; B01J 35/1019; B01J 37/03; B01J 37/0009; C07C 5/2705; C07C 2521/06; C07C 2523/888
USPC ........ 502/308, 313, 318, 324, 304; 585/734, 585/750, 751
See application file for complete search history.

(56) References Cited

U.S. PATENT DOCUMENTS

| | | | |
|---|---|---|---|
| 6,080,904 A | 6/2000 | Chang et al. | |
| 6,124,232 A | 9/2000 | Chang et al. | |
| 6,162,757 A * | 12/2000 | Chang | B01J 21/066 502/349 |
| 6,184,430 B1 * | 2/2001 | Venkatesh | C07C 5/226 585/750 |
| 2008/0032886 A1 * | 2/2008 | Yeh | C10G 45/62 502/118 |
| 2013/0324782 A1 | 12/2013 | Shakun et al. | |
| 2018/0162787 A1 * | 6/2018 | Dakka | C10G 45/58 |

OTHER PUBLICATIONS

Brunauer, S. et al. (1938) "Adsorption of Gases in Multimolecular Layers," *J. Am. Chem. Soc.*, v.60(2), pp. 309-319.

Ghosh, P. et al. (2006) "Development of a Detailed Gasoline Composition-Based Octane Model," *Ind. Eng. Chem. Res.*, v.45(1), pp. 337-345.

Hernandez, M. L. et al. (2006) "Influence of the Synthesis Method on the Nanostructure and Reactivity of Mesoporous Pt/Mn—$WO_x$-$ZrO_2$ Catalysts," *Catlysis Today*, v. 116(2), pp. 169-178.

Hernandez, M. L. et al. (2010) "Optimization of Manganese Content by High-Throughput Experimentation of Pt/$WO_x$—$ZrO_2$—Mn Catalysts," *Catalysis Commun.*, v.11(5), pp. 408-413.

Hernandez, M. L. et al. (2012) "High-Throughput Study of the Iron Promotional Effect over Pt/$WO_x$-$ZrO_2$ Catalysts on the Skeletal Isomerization of n-Hexane," *Applied Catalysis A: General*, v.431-432, pp. 69-78.

Hernandez, M. L. et al. (2019) "Influence of the Incorporation of Fe and Mn on the Nanostructure and Reactivity of Catalysts Based on Tungstated Zironia," *Catlysis Today*, v.360, pp. 72-77.

Masuda, T. et al. (1997) "A Method of Calculating Adsorption Enthalpy Distribution Using Ammonia Temperature-Programmed Desorption Spectrum Under Adsorption Equilibrium Conditions," *Applied Catalysis A: General*, v.165(1-2), pp. 57-72.

J.G Santiesteban et al., "The Role of Platinum in Hexane Isomerization over Pt/FeOy/WOx/ZrO2", J. Catalysis, 2001, pp. 25-33, vol. 202.

Xavier Carrier et al., "The State of the Iron Promoter in Tungstated Zirconia Catalysts", Chem Phys Chem, 2004, pp. 1191-1199, vol. 5.

D.C. Calabro et al., "The Characterization of Tungsten-Oxide-Modified Zirconia Supports for Dual Functional Catalysis", Topics in Catalysis, Feb. 2002, pp. 231-242, vol. 18, Issue 3-4.

David G. Barton et al., "Structure and Electronic Properties of Solid Acids Based on Tungsten Oxide Nanostructures", J. Phys. Chem., 1999, pp. 630-640, vol. 103.

Kiyoyuki Shimizu et al., "NMR study of tungstated zirconia catalyst: acidic properties of tungstated zirconia and influence of tungsten loading", Applied Catalysis A, 2002, pp. 77-87, General 224.

Enrique Iglesia et al., "Selective Isomerization of Alkanes on Supported Tungsten Oxide Acids", J.W. Hightower, W.N. Delgass, E. Iglesia and A.T. Bell (Eds.), Studies in Surface Science and Catalysis, 1996, pp. 533-542, vol. 101.

Makoto Hino et al., "Synthesis of solid superacid of tungsten oxide supported on zirconia and its catalytic action for reactions of butane and pentane", Journal of the Chemical Society, Chemical Communication, 1988, pp. 1259-1260, Issue 18.

Wu Zhou et al., "Identification of active Zr—WOx clusters on a ZrO2 support for solid acid catalysts", Nature Chemistry, Dec. 2009, pp. 722-728.

Ashik, U.P.M., et al., "An Overview of Metal Oxide Nanostructures", Chapter 2, Synthesis of Inorganic Nanomaterials, 2018,19-57.

Kosinov, Nikolay et al., "Engineering of Transition Metal Catalysts Confined in Zeolites", Chem. Mater., 2018, 3177-3198, 30, 10.

* cited by examiner

BIFUNCTIONAL METAL OXIDES AND PARAFFIN ISOMERIZATION THEREWITH

FIELD OF THE INVENTION

The present disclosure relates to paraffin isomerization.

BACKGROUND OF THE INVENTION

Isomerization of linear and monobranched paraffins (alkanes) to form more highly branched paraffins is frequently performed to improve octane rating. Paraffin isomerization to form more highly branched alkanes may be realized using a bifunctional catalyst, such as a mixed metal oxide. Without being bound by theory or mechanism, such catalysts are believed to promote paraffin isomerization through dehydrogenation, protonation to form a carbenium ion, and skeletal rearrangement of the carbenium ion through mechanisms such as those involving a cyclopropyl cation.

In conventional paraffin isomerization processes, a paraffin feed mixture is heated in the presence of hydrogen and a suitable bifunctional catalyst. U.S. Patent Application Publication 2013/0324782 describes one such example of a conventional paraffin isomerization process utilizing a bifunctional catalyst. U.S. Pat. Nos. 6,080,904 and 6,124,232 provide additional details of bifunctional catalysts that are acidic metal oxide catalysts, and paraffin isomerization processes conducted therewith. $C_5$ and $C_6$ normal (linear) paraffins may undergo isomerization readily in such processes. Catalysts such as chlorided alumina, sulfated zirconia, and zeolites may be utilized for isomerizing $C_5$ and $C_6$ paraffins with high selectivity against cracking. $C_{7+}$ normal paraffins, in contrast, become increasingly prone to cracking under the isomerization reaction conditions, particularly at higher reaction temperatures and conversion percentages of the feed mixture, even in the presence of tungstated zirconium catalysts that are less prone to producing cracking. Excessive cracking leads to yield loss of the desired branched paraffins and lower octane numbers. Without being bound by any theory or mechanism, cracking is believed to occur through β-scission of the cation intermediate. During $-scission, $C_5$ and $C_6$ normal paraffins lead to formation of an ethyl cation, a primary carbenium ion that forms with difficulty. In contrast, $C_{7+}$ paraffins may form more stable and more easily generated secondary or tertiary carbenium ions upon β-scission. As such, it can sometimes be difficult to mitigate cracking of $C_{7+}$ paraffins under isomerization reaction conditions, given the favorable thermodynamics for promoting cracking.

U.S. shale oil production is rapidly increasing in volume. Unfortunately, shale oils are typically rich in naphtha hydrocarbons having limited branching, exhibit low octane number values, and provide a short ignition delay, which may make them prone to engine knocking and undesirable for incorporation in fuel blends unless further processed. Branched hydrocarbons having higher octane ratings are generally desirable as blending components for the manufacture of premium gasolines. Conventional isomerization processes are not particularly efficient for increasing the octane number of shale oil naphtha, since $C_7$ and $C_5$ linear paraffins are predominant components of this hydrocarbon resource and tend to undergo extensive cracking instead. Catalytic reforming is also not a particularly desirable option for processing shale oil naphtha due to the rather low energy efficiency of such processes and the frequent low starting aromatic content of this hydrocarbon resource. Although catalytic reforming may be viable for the $C_5+$ components of shale oil naphtha, this approach still leaves a significant fraction of the as-produced hydrocarbon resource without an efficient conversion pathway to form branched paraffins having a high octane number.

SUMMARY OF THE INVENTION

In some aspects, the present disclosure provides compositions comprising a mixed metal oxide. The compositions comprise: a mixed metal oxide that is at least partially crystalline and comprises tungsten, zirconium, and a variable oxidation state metal; wherein the variable oxidation state metal comprises a metal selected from the group consisting of Fe, Mn, Co, Cu, Ce, Ni, and any combination thereof; wherein the mixed metal oxide comprises about 5 wt. % to about 25 wt. % tungsten, about 40 wt. % to about 70 wt. % zirconium, and about 0.01 wt. % to about 5 wt. % variable oxidation state metal, each based on a total mass of the mixed metal oxide; and wherein the mixed metal oxide has a total surface area of about 50 m$^2$/g or greater as measured according to ISO 9277, and at least one of the following: an ammonia uptake of about 0.05 to about 0.3 mmol/g as measured by temperature programmed adsorption/desorption, or a collidine uptake of about 100 μmol/g or greater as measured gravimetrically.

In some or other aspects, the present disclosure provides methods for forming mixed metal oxides. The methods comprise: combining a zirconium source, a tungsten source, and a variable oxidation state metal source in a reaction mixture under alkaline conditions having a pH of about 7.5 or greater; wherein the variable oxidation state metal comprises a metal selected from the group consisting of Fe, Mn, Co, Cu, Ce, Ni, and any combination thereof; obtaining under the alkaline conditions a slurry comprising a co-precipitate reaction product formed from the zirconium source, the tungsten source, and the variable oxidation state metal source; digesting the slurry and forming an amorphous digestion product from the co-precipitate reaction product; and calcining the amorphous digestion product in air at a temperature ranging from about 700° C. to about 900° C. to obtain a mixed metal oxide that is at least partially crystalline and comprises about 5 wt. % to about 25 wt. % tungsten, about 40 wt. % to about 70 wt. % zirconium, and about 0.01 wt. % to about 5 wt. % variable oxidation state metal, each based on a total mass of the mixed metal oxide; wherein the mixed metal oxide has a total surface area of about 50 m$^2$/g or greater as measured according to ISO 9277, and at least one of the following: an ammonia uptake of about 0.05 to about 0.3 mmol/g as measured by temperature programmed adsorption/desorption, or a collidine uptake of about 100 μmol/g or greater as measured gravimetrically.

In still other aspects, the present disclosure provides methods for isomerizing normal paraffins. The methods comprise: heating a mixed metal oxide under hydrogen to form an activated catalyst, the mixed metal oxide being at least partially crystalline and comprising about 5 wt. % to about 25 wt. % tungsten, about 40 wt. % to about 70 wt. % zirconium, and about 0.01 wt. % to about 5 wt. % variable oxidation state metal, wherein the mixed metal oxide is further impregnated with about 0.01 wt. % to about 2 wt. % noble metal, each based on a total mass of the mixed metal oxide plus noble metal; wherein the mixed metal oxide has a total surface area of about 50 m$^2$/g or greater as measured according to ISO 9277, and at least one of the following: an ammonia uptake of about 0.05 to about 0.3 mmol/g as measured by temperature programmed adsorption/desorption, or a collidine uptake of about 100 μmol/g or greater as measured gravimetrically; contacting the activated catalyst with a hydrocarbon feedstock under isomerization reaction conditions, the hydrocarbon feedstock comprising at least one $C_{7+}$ normal alkane; and forming one or more branched alkanes from the at least one $C_{7+}$ normal alkane.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and having the benefit of this disclosure.

DETAILED DESCRIPTION OF THE INVENTION

Figure 1:
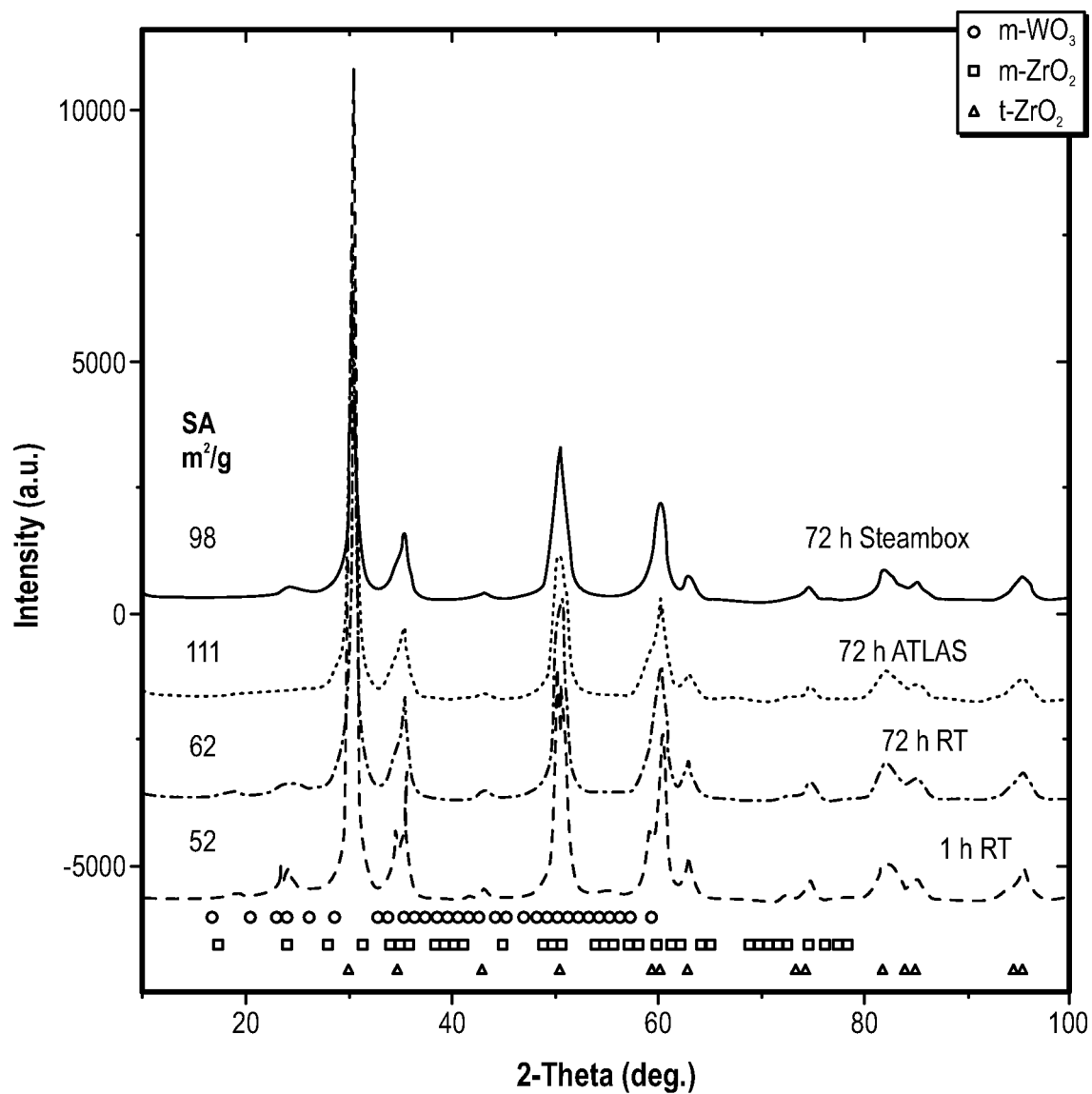
FIG. 1 is a graph showing powder XRD profiles of the samples produced in Examples 5-8 and their corresponding surface areas.

The present disclosure relates to isomerization of paraffins, and, more particularly, compositions comprising mixed metal oxides that may promote paraffin isomerization under conditions that lead to decreased cracking selectivity for $C_{7+}$ normal paraffins. Compositions and methods disclosed herein may be particularly suitable for promoting isomerization of a naphtha feed comprising $C_{7+}$ paraffins that may otherwise undergo excessive cracking under isomerization reaction conditions.

As discussed above, isomerization of normal paraffins may be conducted to increase octane number, but excessive cracking of $C_{7+}$ normal paraffins may be problematic in various respects. To combat the thermodynamic favorability of cracking $C_{7+}$ normal paraffins, isomerization may be conducted at lower temperatures and lower feed mixture conversions, which may be undesirable from a processing efficiency standpoint. As such, it may be difficult to upgrade the octane number of hydrocarbon resources having a significant fraction of normal paraffins, such as naphtha, particularly those with a high fraction of $C_{7+}$ unbranched and monobranched paraffins.

Bifunctional metal oxides (mixed metal oxides) comprising an acidic solid oxide of a Group 4 metal, preferably Ti or Zr, modified with an anion or oxyanion of a Group 6 metal, preferably Mo or W, may be particularly effective for promoting isomerization of paraffins with limited cracking, even though the extent of $C_{7+}$ normal paraffin cracking may still remain undesirably high. Conventional tungstated zirconium catalysts are a representative example. Optionally, a variable oxidation state metal, preferably a first-row transition metal or Ce, may be present in a tungstated zirconium catalyst. Transition metals include metals from Groups 3-12 of the periodic table. Particularly suitable variable oxidation state metals include Fe, Mn, Co, Cu, Ce, Ni, and any combination thereof. The variable oxidation state metal may be Fe in a particular example. Optionally, a first-row transition metal not having a variable oxidation state may be present. The bifunctional metal oxide, which is a mixed metal oxide, may be prepared by co-precipitation, calcination and extrusion to form catalyst particles in a suitable shape. The bifunctional metal oxide may be further impregnated with a Group 8 or 9 metal or a Group 10 metal (noble metal), preferably Pt or Pd, such as through incipient wetness or vacuum infiltration.

The present disclosure provides mixed metal oxides, particularly tungstated zirconium oxides, that differ compositionally from and exhibit different functional performance compared to conventional isomerization catalysts, as well as methods for the production of such mixed metal oxides. Surprisingly, slight changes to the morphology and composition of the mixed metal oxides may afford a significantly decreased extent of cracking under isomerization reaction conditions. The effect is believed to be related to surface area. Accordingly, the present disclosure provides compositions comprising: a mixed metal oxide that is at least partially crystalline and comprises tungsten, zirconium, and a variable oxidation state metal; wherein the variable oxidation state metal comprises a metal that is selected from the group consisting of Fe, Mn, Co, Cu, Ce, Ni, and any combination thereof. The mixed metal oxide comprises about 5 wt. % to about 25 wt. % tungsten, about 40 wt. % to about 70 wt. % zirconium, and about 0.01 wt. % to about 5 wt. % variable oxidation state metal, each based on a total mass of the mixed metal oxide. The mixed metal oxide has a total surface area of about 50 $m^2$/g or greater as measured by nitrogen BET adsorption/desorption isotherms, such as provided in ISO 9277. Further details of BET adsorption/desorption isotherm measurements are provided in *Journal of the American Chemical Society*, 1938, 60 (2), pp 309-319. The mixed metal oxide also exhibits at least one of the following: an ammonia uptake measured by temperature programmed adsorption/desorption, as described in *Applied Catalysis A: General*, 1997, 165, 57-72, of about 0.05 to about 0.3 mmol/g, or a collidine uptake of about 100 μmol/g or greater. Collidine uptake may be measured gravimetrically under the same temperature and pressure conditions of ammonia uptake, but without measuring desorption. Ammonia uptake measured by temperature programmed adsorption/desorption may be a preferred characterization method. Such bifunctional metal oxides may be effective to promote isomerization of paraffins, particularly $C_{7+}$ normal and monobranched paraffins, with a decreased extent of cracking, particularly compared to conventional tungstated zirconium catalysts.

Further, the present disclosure provides methods of making the compositions described above. Such methods may comprise: combining a zirconium source, a tungsten source, and a variable oxidation state metal source in a reaction mixture under alkaline conditions having a pH of about 7.5 or greater; wherein the variable oxidation state metal source comprises a metal selected from the group consisting of Fe, Mn, Co, Cu, Ce, Ni, and any combination thereof; obtaining under the alkaline conditions a slurry comprising a co-precipitate reaction product formed from the zirconium source, the tungsten source, and the variable oxidation state metal source; digesting the slurry at a digestion temperature and forming an amorphous digestion product from the co-precipitate reaction product; and calcining the amorphous digestion product in air at a temperature ranging from about 700° C. to about 900° C. to obtain a mixed metal oxide that is at least partially crystalline and comprises about 5 wt. % to about 25 wt. % tungsten, about 40 wt. % to about 70 wt. % zirconium, and about 0.01 wt. % to about 5 wt. % variable oxidation state metal, each based on a total mass of the mixed metal oxide. The mixed metal oxide has a total surface area of about 50 m$^2$/g or greater, and at least one of the following: an ammonia uptake of about 0.05 to about 0.3 mmol/g, or a collidine uptake of about 100 μmol/g or greater. Measurement conditions for these values are specified above. Herein, the reaction mixture may be formed by combining a first solution comprising the tungsten source, and a second solution comprising the zirconium source and the variable oxidation state metal source in an alkaline solution having a pH of about 9 to about 10.

Furthermore, the reaction mixture may be formed to promote co-precipitation in an alkaline solution, such as in the presence of ammonium hydroxide or an alkylammonium hydroxide. A hydroxide precipitate may be formed initially from the Group 4 salt (e.g., an acidic solution of Zr) and the anion or oxyanion comprising the Group 6 metal (e.g., a basic solution of W). The hydroxide precipitate may be amorphous and have a very high surface area. The hydroxide precipitate may then be converted into a mixed metal oxide through calcination, in which the surface area is considerably lower following calcination. Calcination may take place in air at a temperature of about 600° C. to about 900° C., or about 650° C. to about 850° C., or about 700° C. to about 800° C., for example.

The present disclosure advantageously demonstrates that control of the co-precipitation conditions, reagent concentrations, digestion temperature conditions, and calcination temperatures, among other factors, may afford increased surface area, which upon extrusion and noble metal impregnation, may surprisingly increase $C_5$-$C_{30}$ alkane isomerization, such as $C_5$-$C_7$ alkane isomerization, while suppressing cracking of $C_{7+}$ normal and monobranched paraffins. In addition to suppressing cracking of paraffins in the $C_5$-$C_{30}$ range, such as in the $C_5$-$C_7$ range, for making gasoline hydrocarbons, the present disclosure may also facilitate decreased cracking when isomerizing larger paraffins in the $C_5$-$C_{30}$ range or $C_{10}$-$C_{30}$ range, for example. Hydrocarbons within this size range may be useful as diesel components or lubricants and may similarly benefit from isomerization to decrease melting points and alter pour points, cloud points or viscosity indices, as needed for particular end use applications. As such, the present disclosure offers broad applicability beyond just increasing the octane number of gasoline hydrocarbons.

All numerical values within the detailed description and the claims herein are modified by "about" or "approximately" with respect to the indicated value, and take into account experimental error and variations that would be expected by a person having ordinary skill in the art. Unless otherwise indicated, ambient temperature (room temperature) is about 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A," and "B."

For the purposes of the present disclosure, the new numbering scheme for groups of the Periodic Table is used. In said numbering scheme, the groups (columns) are numbered sequentially from left to right from 1 through 18.

As used herein, the term "hydrocarbon" refers to (i) any compound consisting of hydrogen and carbon atoms or (ii) any mixture of two or more such compounds in (i). The term "$C_n$ hydrocarbon," where n is a positive integer, means (i) any hydrocarbon compound comprising carbon atom(s) in its molecular structure having n total carbon atom, or (ii) any mixture of two or more such hydrocarbon compounds in (i). Any degree of unsaturated may be present in such $C_n$ hydrocarbons. Thus, a $C_2$ hydrocarbon may refer to ethane, ethylene, acetylene, or mixtures of at least two of these hydrocarbons at any proportion. The term "$C_{n+}$ hydrocarbon" means (i) any hydrocarbon compound comprising n or greater carbon atom(s) in its molecular structure, or (ii) any mixture of two or more such hydrocarbon compounds in (i). The term "$C_{n-}$ hydrocarbon" means (i) any hydrocarbon compound comprising n carbon atoms or less in its molecular structure, or (ii) any mixture of two or more such hydrocarbon compounds in (i).

As used herein, the term "naphtha" refers to $C_4$-$C_{12}$ hydrocarbons, particularly $C_4$-$C_{12}$ saturated hydrocarbons.

As used herein, the terms "paraffin," "alkane," and "saturated hydrocarbon" are synonymous with one another and refer to hydrocarbons having a formula of $C_nH_{2n+2}$.

As used herein, the terms "linear" and "normal" are synonymous with one another and refer to hydrocarbons without side-chain branches.

As used herein, the term "cracking" refers to the conversion of a given hydrocarbon molecule into two smaller hydrocarbon molecules.

As used herein, the term "isomerization" refers to a skeletal rearrangement of a hydrocarbon, particularly conversion of a normal paraffin into a branched paraffin.

As used herein, the term "weight hour space velocity" (WHSV) refers to a measure of the weight of a feed mixture flowing per unit weight of a catalyst per hour.

As used herein, the term "liquid hour space velocity" (LHSV) refers to a measure of the volume of a feed mixture flowing per unit volume of a catalyst per hour.

As used herein, the term "variable oxidation state metal" refers to a metal having two or more accessible oxidation states other than a zero oxidation state.

As used herein, the term "total surface area" refers to the total specific external and internal surface area of disperse or porous solids (microporous materials), which is obtained by measuring the amount of physically adsorbed $N_2$ adsorption/desorption isotherms, such as specified in ISO 9277.

As used herein, the term "ammonia uptake" refers to the measurement of temperature programmed ammonia adsorption/desorption of disperse or porous solids (microporous materials), which is measured as described in *Applied Catalysis A: General*, 1997, 165, 57-72.

As used herein, the term "collidine uptake" refers to the millimoles of collidine (a type of catalyst poison) absorbed per gram of sample. In a non-limiting example, the sample may be dried under nitrogen flow at 200° C. for 60 minutes on a Thermogravametric Analyzer (Model Q5000, manufactured by TA Instruments, New Castle, Del.) before exposing the sample to collidine and measuring the amount of adsorbed collidine gravimetrically.

As used herein, the term "digestion" refers to a thermal treatment taking place by heating a solid in a solvent in which an impurity species may be soluble but the majority of the solid is not. Digestion may allow for equilibration of species to take place, along with ripening of particles of the insoluble solid. The digestion conditions, including the digestion temperature, may impact the surface area and the porosity of a mesoporous material obtained therefrom.

Compositions and Methods for Making the Same

Compositions of the present disclosure may include an acidic solid oxide (mixed metal oxide) of a Group 4 metal, preferably Ti or Zr, modified with an anion or oxyanion of a Group 6 metal, preferably Mo or W. Optionally, a variable oxidation state metal may be present, wherein the variable oxidation state metal comprises a metal that is selected from the group consisting of Fe, Mn, Co, Cu, Ce, Ni, and any combination thereof. The compositions may be prepared by co-precipitation, calcination and extrusion to form catalyst particles in a suitable shape. Extrudates may be prepared with or without a binder being present. The compositions may be further impregnated with a Group 8 or 9 metal or a Group 10 metal (noble metal), preferably Pt or Pd, such as through incipient wetness or vacuum infiltration. Incorporation of a noble metal may promote catalytic activity toward paraffin isomerization.

In more particular examples, the mixed metal oxide may be impregnated with a noble metal, the noble metal being present at about 0.01 wt. % to about 2 wt. %, or about 0.05 wt. % to about 1.8 wt. %, or about 0.1 wt. % to about 1.6 wt. %, or about 0.2 wt. % to about 1.4 wt. %, or about 0.3 wt. % to about 1.2 wt. %, or about 0.4 wt. % to about 1 wt. %, based on total mass of the mixed metal oxide plus noble metal. The noble metal may comprise at least one noble metal selected from the group consisting of Pt, Pd, Rh, and any combination thereof. Preferably, the noble metal comprises Pt.

The mixed metal oxides of the present disclosure may comprise Zr as the Group 4 metal and W as the Group 6 metal. Such mixed metal oxides may be referred to as tungstated zirconium oxide catalysts or tungstated zirconium catalysts herein, which may comprise about 5 wt. % to about 25 wt. % W, about 40 wt. % to about 70 wt. % Zr, and about 0.01 wt. % to about 5 wt. % variable oxidation state metal, preferably Fe, each based upon total mass of the mixed metal oxide. In some cases, the mixed oxide may comprise about 9 wt. % to about 20 wt. % W, about 40 wt. % to 70 wt. % Zr, and about 0.01 wt. % to 2 wt. % variable oxidation state metal, each based on total mass of the mixed metal oxide. Preferably, the mixed metal oxide may comprise about 0.5 wt. % to 0.7 wt. % variable oxidation state metal, based on total mass of the mixed metal oxide.

The variable oxidation state metal may be selected from the group consisting of Fe, Mn, Cu, Co, Ce, Ni, and any combination thereof. In at least one embodiment, the variable oxidation state metal may comprise Fe.

The mixed metal oxide, when activated, may be effective to isomerize n-heptane at a conversion:cracking yield ratio of about 10 or greater at about 10% or less cracking yield. Cracking yield may be determined by the mass of $C_1$-$C_4$ hydrocarbons produced upon isomerizing a $C_5$+ alkane feed mixture.

Herein, the mixed metal oxide may have a total surface area of about 75 $m^2/g$ or above or about 85 $m^2/g$ or above. In more particular examples, the surface area of the mixed metal oxides may range from about 50 $m^2/g$ to about 150 $m^2/g$, or about 60 $m^2/g$ to about 120 $m^2/g$, or about 70 $m^2/g$ to about 110 $m^2/g$. Such measurements may be made by $N_2$ BET adsorption/desorption isotherms, particularly according to ISO 9277.

The mixed metal oxides may have a tungsten (W) surface density, measured as W atoms/$nm^2$, ranging from about 2 to about 20 (or about 2.2 to about 18, or about 2.4 to about 16, or about 2.4 to about 14, or about 2.6 to about 12, or about 2.8 to about 10, or about 3 to about 8, or about 4 to about 12, or about 5 to about 7). The tungsten (W) surface density can be calculated from (a) the measured W content (wt. %) obtained by X-ray fluorescence and (b) the measured surface area obtained by $N_2$ BET.

The mixed metal oxide may have an X-ray diffraction peak height ratio ranging from 0 to about 5 for monoclinic tungsten oxide (m-$WO_3$) relative to monoclinic zirconium oxide (m-$ZrO_2$). m-$WO_3$ is synonymous with monoclinic tungsten oxide. m-$ZrO_2$ is synonymous with monoclinic zirconium oxide. More preferably, the X-ray diffraction peak height ratio may range from 0 to 3. The X-ray diffraction peaks are expressed as 2θ values and are determined using Cu Kα radiation. The following approximate 2θ peak positions are characteristic: m-$WO_3$=24.4° and m-$ZrO_2$=28.4°. Tetragonal $ZrO_2$ (t-$ZrO_2$) may be found an at approximate 2θ peak position of 30.2°. A higher ratio of m-$WO_3$ to m-$ZrO_2$ may be associated with less W becoming active.

The compositions of the present disclosure may further comprise a binder combined with the mixed metal oxide. Up to about 50 wt. % binder may be present. The binder may comprise at least one substance selected from the group consisting of a W/Zr oxide, a W/Zr hydroxide, a W oxide, a W hydroxide, a Zr oxide, a Zr hydroxide, an Fe oxide, an Fe hydroxide, a Ti oxide, a Ti hydroxide, silica, silica alumina, a titania silica, an aluminum oxide, an aluminum hydroxide, and any combination thereof. Extruded samples may also be self-bound as well (i.e., no binder being present).

When preparing the compositions by co-precipitation and calcination, suitable sources of the Group 4 metal may include, for example, Group 4 salts (e.g., Zr salts) such as chlorides, oxychlorides, nitrates, acetates, alkoxides, and the like. Ti and/or Y may also be included in combination with Zr. Suitable sources of the anion or oxyanion comprising the Group 6 metal, preferably W, may include, for example, ammonium or alkali metal metatungstate (Na or K), ammonium or alkali metal metamolybdate (Na or K), tungsten chloride, molybdenum chloride, tungstic acid, molybdic acid, and any combination thereof.

Co-precipitation may take place in an alkaline solution, such as in the presence of ammonium hydroxide or an alkylammonium hydroxide. A hydroxide precipitate may be formed initially from the Group 4 salt and the anion or oxyanion comprising the Group 6 metal. The hydroxide precipitate may be amorphous and have a high surface area. The hydroxide precipitate may then be converted into a mixed metal oxide through calcination, in which the surface area is considerably lower following calcination. Calcination may take place in air at a temperature of about 600° C. to about 900° C., or about 650° C. to about 850° C., or about 700° C. to about 800° C., for example.

In at least one embodiment, after co-precipitation, the resulting powder is (a) washed with water and dried at a temperature ranging from about 110° C. to 140° C. (e.g., 120° C.), (b) washed with an ammonium salt solution, (c) calcined at a temperature ranging from about 600° C. to about 900° C., (d) formed into a desired shape, (e) washed with an ammonium salt solution, and (f) calcined at 600° C. or less. A metal (e.g., a noble metal) may then be added, and the metal may be oxidized to remove ligands and form metal oxide. The metal may then be reduced prior to conducting paraffin isomerization. Tungsten and other components in the composition may also undergo reduction in this process.

Before calcining, the hydroxide precipitate may be digested to form an amorphous digestion product. Digestion may be conducted at a temperature from about 25° C. to about 200° C., preferably from about 40° C. to about 150° C. or from about 60° C. to about 120° C. Surprisingly, the digestion temperature may significantly impact the surface area that is obtained following calcination.

A noble metal precursor may be impregnated in the mixed metal oxide following formation thereof through calcination. Suitable techniques for incorporating the noble metal precursor may include incipient wetness impregnation, vacuum infiltration impregnation, or any combination thereof. The noble metal precursor may comprise at least one noble metal selected from the group consisting of Pt, Pd, Rh, and any combination thereof. In the case of Pt, the noble metal precursor may comprise a water-soluble metal complex selected from the group consisting of $(NH_3)_4Pt(NO_3)_2$, $(NH_3)_4Pt(OH)_2$, $(NH_3)_4PtCl_2$, $H_2PtCl_6$, and any combination thereof. Other mixed ligand complexes may also be suitable.

Once formed through calcination, the mixed metal oxide may be impregnated with a Group 8-10 metal (via a suitable noble metal precursor), preferably a noble metal such as Pt or Pd, or first extruded to form the mixed metal oxide into a suitable shape, such as pellets, cylinders, lobed structures, and the like. Extrusion may be conducted in a range of possible shapes and sizes such as 1/10" cylinders, 1/8" cylinders, quadrulobes, and trilobes, 1/16" cylinders, quadrulobes, and trilobes, and 1/20" cylinders, quadrulobes, and trilobes. Extrusion may be performed in the presence of an extrusion aid, such as cellulose, methylcellulose, hydrogenated or ethoxylated oils (e.g., vegetable, coconut, soy, or palm), and/or polymers (e.g., PVA). Optionally, the mixed metal oxide may be combined with a binder such as silica, alumina, or other suitable binder prior to performing extrusion. In some examples, extrusion of calcined powders may be carried out using oxides or hydroxides of silica, titania, lanthana, yttria, zirconia, tungsten, iron, tungsten/zirconia, and mixture thereof as a binder. Accordingly, methods of the present disclosure may further comprise: forming an extrudate from the mixed metal oxide, optionally wherein the mixed metal oxide may be co-extruded with a binder to form the extrudate. Typical composition ranges for extrusion are about 0:100 to 50:50 binder:mixed metal oxide on a weight basis, preferably about 0:100 to 35:65 or about 0:100 to 25:75. Following extrusion, calcination may again be conducted, such as at a temperature of about 600° C. or below.

In at least one embodiment, extrusion may be accomplished by either (a) forming dried powder of the mixed metal oxide, and calcining the dried powder at a temperature ranging from about 600° C. to about 900° C. to form an active phase, or (b) first calcining the powder to form an active phase, forming and calcining at a temperature of about 600° C. or less.

Once a mixed metal oxide has been formed, optionally following extrusion, the mixed metal oxide may be impregnated with a metal suitable to promote isomerization in the presence of hydrogen gas, particularly through a dehydrogenation/hydrogenation mechanism. Group 8-10 metals may be effective in this regard. Impregnation may be conducted using incipient wetness or vacuum infiltration techniques, for example. Preferably, the metal suitable to promote isomerization may be a noble metal, such as Pt or Pd. In the case of Pt, suitable sources for introducing this metal may include chloroplatinic acid, tetrammineplatinum complexes, platinum chloride, and any combination thereof. After impregnation of the mixed metal oxide has taken place, the metal suitable to promote isomerization may likewise be converted into an oxide form of the metal through calcination, such as at an temperature ranging from about 280° C. to about 360° C.

Isomerization Methods

Further, methods of the present disclosure may comprise: heating a mixed metal oxide under hydrogen to form an activated catalyst, the mixed metal oxide being at least partially crystalline and comprising about 5 wt. % to about 25 wt. % tungsten, about 40 wt. % to about 70 wt. % zirconium, and about 0.01 wt. % to about 5 wt. % variable oxidation state metal, wherein the mixed metal oxide is further impregnated with about 0.01 wt. % to about 2 wt. % noble metal, each based on a total mass of the mixed metal oxide plus noble metal; wherein the mixed metal oxide has a total surface area of about 50 $m^2/g$ or greater, and at least one of the following: an ammonia uptake of about 0.05 to about 0.3 mmol/g, or a collidine uptake of about 100 μmol/g or greater; contacting the activated catalyst with a hydrocarbon feedstock under isomerization reaction conditions, the hydrocarbon feedstock comprising at least one $C_{7+}$ normal alkane; and forming one or more branched alkanes from the at least one $C_{7+}$ normal alkane.

In at least one embodiment, the activated catalyst is a bifunctional metal oxide catalyst (mixed metal oxide catalyst) effective to promote isomerization of a normal paraffin, such as defined by the compositions described. Mixed metal oxides may be impregnated with a noble metal to form suitable bifunctional metal oxide catalysts.

The hydrocarbon feedstock may comprise at least $C_5$-$C_{30}$ normal paraffins, such as $C_5$-$C_7$ normal paraffins, or $C_{7+}$ normal paraffins and/or monobranched paraffins. The hydrocarbon feedstock may also comprise $C_{7+}$ normal paraffins, such as $C_5$-$C_{30}$ normal paraffins, as well as monobranched paraffins (e.g., a $C_5$ monobranched paraffin, a $C_6$ monobranched paraffin or a $C_{7+}$ monobranched paraffin), a $C_5$ normal paraffin, a $C_6$ normal paraffin, or any combination thereof. Thus, particular hydrocarbon feedstocks suitable for use in the disclosure herein may comprise normal or monobranched $C_5$ paraffins, normal or monobranched $C_6$ paraffins, and normal or monobranched $C_7$ paraffins. Optionally, at least some normal or monobranched $C_5$ paraffins may be present in such hydrocarbon feedstocks as well. Other suitable hydrocarbon feedstocks suitable for use in the disclosure herein may comprise $C_{10}$-$C_{10}$ normal paraffins or monobranched paraffins. Any of the foregoing may further comprise one or more aromatic compounds as well.

Optionally, one or more naphthenic compounds may be combined with any of the foregoing hydrocarbon feedstocks. By including one or more naphthenic compounds as a co-feed, the incidence of cracking may be lowered still further. About 10 wt. % or more naphthenic compounds may be present in combination with the hydrocarbon feedstock. Suitable naphthenic compounds may include branched naphthenic compounds such as methylcyclopentane (MCP), methylcyclohexane (MCH), or any combination thereof. Other suitable branched naphthenic compounds such as ethylcylopentane, propylcyclopentane, 1,1-dimethylcyclopentane, 1,1-dimethylcyclohexane, ethylcyclohexane, propylcyclohexane, and the like may also be suitable for use in the disclosure herein. Bicyclic naphthenic compounds may be suitable as well. In general, any naphthenic compound that may form a tertiary carbenium ion under isomerization reaction conditions may be used effectively in the disclosure herein.

The activated catalyst may be contacted with the hydrocarbon feedstock under one or more of the following isomerization reaction conditions: a temperature ranging from about 150° C. to about 210° C., preferably a temperature ranging from about 150° C. to about 190° C.; a mole ratio of hydrogen to hydrocarbon feedstock ranging from about 1:1 to about 3:1; a pressure ranging from about 100 psig to about 350 psig; and a liquid hourly space velocity ranging from about 0.5 h$^{-1}$ to about 6 h$^{-1}$. Hydrogen partial pressures may range from about 50 kPa to about 2000 kPa, for example. In particular examples, the isomerization reaction conditions may include a liquid hour space velocity of about 6 hr$^{-1}$ or less, or about 5 hr$^{-1}$ or less, or about 4 hr$^{-1}$ or less, preferably a LHSV ranging from about 2 hr$^{-1}$ to about 5 hr$^{-1}$.

The isomerization reaction conditions may be such that the isomerization reaction is carried out in the gas phase, a supercritical phase, or a liquid phase.

The isomerization reaction conditions may afford about 95% or less conversion, or about 90% or less conversion, or about 85% or less conversion, or about 80% or less conversion, or about 75% or less conversion, or about 70% or less conversion of the $C_5$-$C_7$ normal paraffins. Particular examples may afford about 70% to about 90% conversion of $C_5$-$C_7$ or $C_{7+}$ normal paraffins. Cracking yields for n-heptane may be about 10 wt. % or less, and the ratio of n-heptane conversion:cracking yield may be about 10 or more, such as about 10 to about 25, or about 10 to about 20.

Embodiments disclosed herein include:

A. Mixed metal oxide compositions. The compositions comprise: a mixed metal oxide that is at least partially crystalline and comprises tungsten, zirconium, and a variable oxidation state metal; wherein the variable oxidation state metal comprises a metal selected from the group consisting of Fe, Mn, Co, Cu, Ce, and Ni; wherein the mixed metal oxide comprises about 5 wt. % to about 25 wt. % tungsten, about 40 wt. % to about 70 wt. % zirconium, and about 0.01 wt. % to about 5 wt. % variable oxidation state metal, each based on a total mass of the mixed metal oxide; and wherein the mixed metal oxide has a total surface area of about 50 m$^2$/g or greater as measured according to ISO 9277, and at least one of the following: an ammonia uptake of about 0.05 to about 0.3 mmol/g as measured by temperature programmed adsorption/desorption, or a collidine uptake of about 100 μmol/g or greater as measured gravimetrically.

B. Methods for making mixed metal oxide compositions. The method comprising: combining a zirconium source, a tungsten source, and a variable oxidation state metal source in a reaction mixture under alkaline conditions having a pH of about 7.5 or greater; wherein the variable oxidation state metal comprises a metal selected from the group consisting of Fe, Mn, Co, Cu, Ce, and Ni; obtaining under the alkaline conditions a slurry comprising a co-precipitate reaction product formed from the zirconium source, the tungsten source, and the variable oxidation state metal source; digesting the slurry and forming an amorphous digestion product from the co-precipitate reaction product; and calcining the amorphous digestion product in air at a temperature ranging from about 700° C. to about 900° C. to obtain a mixed metal oxide that is at least partially crystalline and comprises about 5 wt. % to about 25 wt. % tungsten, about 40 wt. % to about 70 wt. % zirconium, and about 0.01 wt. % to about 5 wt. % variable oxidation state metal, each based on a total mass of the mixed metal oxide; wherein the mixed metal oxide has a total surface area of about 50 m$^2$/g or greater as measured according to ISO 9277, and at least one of the following: an ammonia uptake of about 0.05 to about 0.3 mmol/g as measured by temperature programmed adsorption/desorption, or a collidine uptake of about 100 μmol/g or greater as measured gravimetrically.

C. Methods for making branched alkanes. The methods comprise: heating a mixed metal oxide under hydrogen to form an activated catalyst, the mixed metal oxide being at least partially crystalline and comprising about 5 wt. % to about 25 wt. % tungsten, about 40 wt. % to about 70 wt. % zirconium, and about 0.01 wt. % to about 5 wt. % variable oxidation state metal, wherein the mixed metal oxide is further impregnated with about 0.01 wt. % to about 2 wt. % noble metal, each based on a total mass of the mixed metal oxide plus noble metal; wherein the mixed metal oxide has a total surface area of about 50 m$^2$/g or greater as measured according to ISO 9277, and at least one of the following: an ammonia uptake of about 0.05 to about 0.3 mmol/g as measured by temperature programmed adsorption/desorption, or a collidine uptake of about 100 μmol/g or greater; contacting the activated catalyst with a hydrocarbon feedstock under isomerization reaction conditions, the hydrocarbon feedstock comprising at least one $C_{7+}$ normal alkane; and forming one or more branched alkanes from the at least one $C_{7+}$ normal alkane.

Embodiments A, B, and C may have one or more of the following elements in any combination:

Element 1: wherein the mixed metal oxide is impregnated with a noble metal, the noble metal being present at about 0.01 wt. % to about 2 wt. % based on total mass of the mixed metal oxide plus noble metal.

Element 2: wherein the noble metal comprises at least one noble metal selected from the group consisting of Pt, Pd, Rh, and any combination thereof.

Element 3: wherein the mixed metal oxide, when activated, is effective to isomerize n-heptane at a conversion:cracking yield ratio of about 10 or greater at about 10% or less cracking yield.

Element 4: wherein the mixed metal oxide, when activated, is effective to isomerize n-heptane at a conversion:cracking yield ratio of about 10 to about 15 at about 10% or less cracking yield.

Element 5: wherein the mixed metal oxide has a total surface area ranging from about 60 m$^2$/g to about 130 m$^2$/g.

Element 6: wherein the mixed metal oxide has a tungsten surface density, measured as W atoms/nm$^2$, ranging from about 2 to about 20.

Element 7: wherein the mixed metal oxide has an X-ray powder diffraction peak height ratio ranging from 0 to about 5 for monoclinic tungsten oxide (m-WO$_3$) relative to monoclinic zirconium oxide (m-ZrO$_2$).

Element 8: wherein the mixed metal oxide comprises about 9 wt. % to about 20 wt. % tungsten, about 40 wt. % to 70 wt. % Zr, and about 0.01 wt. % to 2 wt. % variable oxidation state metal, each based on total mass of the mixed metal oxide.

Element 9: wherein the mixed metal oxide comprises about 0.5 wt. % to 0.7 wt. % variable oxidation state metal, based on total mass of the mixed metal oxide.

Element 10: wherein the variable oxidation state metal is selected from the group consisting of Fe, Mn, Cu, Ce, and any combination thereof.

Element 11: wherein the variable oxidation state metal comprises Fe.

Element 12: wherein the composition further comprises a binder combined with the mixed metal oxide.

Element 13: wherein the reaction mixture is formed by combining a first solution comprising the tungsten source, and a second solution comprising the zirconium source and the variable oxidation state metal source in an alkaline solution having a pH of about 9 to about 10.

Element 14: wherein the method further comprises, after calcining, introducing a noble metal precursor to the mixed metal oxide by incipient wetness impregnation, vacuum infiltration impregnation, or any combination thereof.

Element 15: wherein the noble metal precursor comprises a water-soluble metal complex selected from the group consisting of $(NH_3)_4Pt(NO_3)_2$, $(NH_3)_4Pt(OH)_2$, $(NH_3)_4PtCl_2$, $H_2PtCl_6$, and any combination thereof.

Element 16: further comprising forming an extrudate from the mixed metal oxide.

Element 17: wherein the mixed metal oxide is co-extruded with a binder to form the extrudate.

Element 18: wherein the binder comprises at least one substance selected from the group consisting of a W/Zr oxide, a W/Zr hydroxide, a W oxide, a W hydroxide, a Zr oxide, a Zr hydroxide, an Fe oxide, an Fe hydroxide, a Ti oxide, a Ti hydroxide, silica, silica alumina, a titania silica, an aluminum oxide, an aluminum hydroxide, and any combination thereof.

Element 19: wherein the isomerization reaction conditions comprise one or more of the following: a temperature ranging from about 150° C. to about 210° C.; a ratio of hydrogen to hydrocarbon feedstock ranging from about 1:1 to about 3:1; a pressure ranging from about 150 psig to about 350 psig; and a liquid hourly space velocity ranging from about 0.5 $h^{-1}$ to about 6 $h^{-1}$.

By way of non-limiting example, exemplary combinations applicable to A include, but are not limited to: 1 or 2, and 3; 1 or 2, and 4; 1 or 2, and 5; 1 or 2, and 6; 1 or 2, and 6 and 7; 1 or 2, and 7; 1 or 2, and 8; 1 or 2, and 6-8; 1 or 2, and 7 and 8; 1 or 2, and 9; 1 or 2, and 6-9; 1 or 2, and 10; 1 or 2, and 11; 1 or 2, and 12; 1 or 2, and 4 and 5; 1 or 2, and 6; 7 and 8; 9 and 10; and 11 and 12.

By way of non-limiting example, exemplary combinations applicable to B include, but are not limited to: 1 or 2, and 3; 1 or 2, and 4; 1 or 2, and 5; 1 or 2, and 6; 1 or 2, and 6 and 7; 1 or 2, and 7; 1 or 2, and 8; 1 or 2, and 6-8; 1 or 2, and 7 and 8; 1 or 2, and 9; 1 or 2, and 6-9; 1 or 2, and 11; 1 or 2, and 12; 1 or 2, and 13; 1 or 2, and 14; 1 or 2, and 15; 1 or 2, and 16; 1 or 2, and 17; 1 or 2, and 18; 1 or 2, and 13 and 14; 1 or 2, and 16; 13 and 14; 13 and 15; and 13 and 16, 1 or 2, and 16, and 17, and 18.

By way of non-limiting example, exemplary combinations applicable to C include, but are not limited to: 1 or 2, and 3; 1 or 2, and 4; 1 or 2, and 5; 1 or 2, and 6; 1 or 2, and 6 and 7; 1 or 2, and 7; 1 or 2, and 8; 1 or 2, and 6-8; 1 or 2, and 7 and 8; 1 or 2, and 9; 1 or 2, and 6-9; 1 or 2, and 11; 1 or 2, and 12; 1 or 2, and 13; 1 or 2, and 14; 1 or 2, and 15; 1 or 2, and 16; 1 or 2, and 17; 1 or 2, and 18; 1 or 2, and 13 and 14; 1 or 2, and 16; 13 and 14; 13 and 15; and 13 and 16, 4 or 5, and 19.

To facilitate a better understanding of the present disclosure, the following examples of preferred or representative embodiments are given. In no way should the following examples be read to limit, or to define, the scope of the present disclosure.

EXAMPLES

Example 1: Initial reagent concentrations and reaction conditions. Preparation of solution A: In a beaker, 71.7 grams of concentrated $NH_4OH$ and 14.9 grams of $(NH_4)_6H_2W_{12}O_{40}\cdot xH_2O$ (66.9% W) (ammonium metatungstate, AMT) were combined with stirring in 400 ml of $H_2O$ and heated at 60° C. Preparation of solution B: 138 grams of $ZrOCl_2\cdot xH_2O$ and 2.1 grams of $FeSO_4$ were dissolved in 400 ml of $H_2O$ and heated at 60° C. In a separate vessel (the vessel in which the precipitation was to occur), 839.4 grams of de-ionized water was added, and the pH was adjusted to 9-10 with the addition of $NH_4OH$. The alkaline solution was then stirred at 40° C. While stirring, solutions A and B were added to the alkaline solution at 10 ml/minute. After the complete addition of solutions A and B, the resulting slurry was stirred for an hour at 40° C. Upon completion of the co-precipitation, the slurry was transferred to another container (e.g., polypropylene bottle or Teflon bottle), and digested for 72 hours at 100° C. After digestion, the resulting powder was filtered and washed with water. The powder at this point may or may not be washed with $NH_4NO_3$, washed with additional water, and dried at 120° C. The powder was then calcined in air at a temperature ranging from 700° C. to 850° C. in order to prepare the active oxide form of the powder, which was composed of 0.61 wt. % Fe, 15.4 wt. % W, and 54.0 wt. % Zr on average. The powder X-ray diffraction pattern (not shown) contained primarily tetragonal zirconium oxide and possibly small amounts of monoclinic tungsten oxide. The average peak height ratio from powder X-ray diffraction of the monoclinic tungsten oxide: monoclinic zirconium oxide was 0.55 after calcination at 750° C. At higher calcination temperatures (>800° C.), the amount of monoclinic tungsten oxide and monoclinic zirconium oxide increased. The resulting surface area was 89 $m^2/g$, and the $NH_3$ uptake was 0.16 mmol/g, each on average.

Example 2: Doubled reagent concentration during co-precipitation. This example was conducted in a similar manner to Example 1, except at a doubled scale in solutions A and B. Solutions A and B were added to the same volume of alkaline solution for co-precipitation. Preparation of solution A: In a beaker, 143.5 grams of concentrated $NH_4OH$ and 29.8 grams of $(NH_4)_6H_2W_{12}O_{40}\cdot xH_2O$ (66.9% W) (ammonium metatungstate, AMT) were stirred in 400 ml of $H_2O$ and heated at 60° C. Preparation of solution B: 276 grams of $ZrOCl_2\cdot xH_2O$ and 4.2 grams of $FeSO_4$ were dissolved in 400 ml of $H_2O$ and heated at 60° C. In a separate vessel (the vessel in which precipitation was to occur), 839.4 grams of de-ionized water was added, and the pH was adjusted to 9-10 with $NH_4OH$. The alkaline solution was stirred in the vessel at 40° C. While stirring, solutions A and B were added to the alkaline solution at 10 ml/minute. After the complete addition of solutions A and B, the slurry was stirred for an hour at 40° C. Upon completion of the co-precipitation, the slurry was transferred to another container (e.g., polypropylene bottle or Teflon bottle), and then digested for 72 hours at 100° C. After digestion, the resulting powder was filtered and washed with water. The powder may or may not be washed with $NH_4NO_3$ at this point and then washed with additional water, and dried at 120° C. The powder was then calcined in air at a temperature ranging from 700° C. to 850° C. to prepare the active oxide form of the powder, which was composed of 0.65 wt. % Fe, 16.4 wt. % W, and 54.1 wt. % Zr on average. The powder X-ray diffraction pattern (not shown) contained primarily tetragonal zirconium oxide and possibly small amounts of monoclinic tungsten oxide. The average peak height ratio from the powder X-ray diffraction of the monoclinic tungsten oxide:monoclinic zirconium oxide was 0.53 after calcination at 750° C. At higher calcination temperatures (>800° C.), the amount of monoclinic tungsten oxide and monoclinic zirconium oxide increased. The resulting surface area was 96 $m^2/g$, and the $NH_3$ uptake was 0.17 mmol/g, each on average.

Example 3: Doubled reagent concentration during co-precipitation and co-precipitation at 25° C. This example was conducted in the same manner as Example 2, except co-precipitation was conducted at 23-25° C. for one hour. The resulting active oxide was composed of 0.51 wt. % Fe, 8.9 wt. % W, and 64.1 wt. % Zr on average. The powder X-ray diffraction pattern (not shown) contained primarily tetragonal zirconium oxide and possibly small amounts of monoclinic tungsten oxide. The average peak height ratio from powder X-ray diffraction of the monoclinic tungsten oxide:monoclinic zirconium oxide was 0.44 after calcination at 750° C. At higher calcination temperatures (>800° C.), the amount of monoclinic tungsten oxide and monoclinic zirconium oxide increased. The resulting surface area was 93 m$^2$/g, and the NH$_3$ uptake was 0.19 mmol/g, each on average.

Example 4: Doubled reagent concentration during co-precipitation, co-precipitation at 25° C. and 25° C. digestion. This example was conducted in the same manner as Example 2, except co-precipitation was conducted at 23-25° C., and digestion was conducted at 25° C. The active oxide form of the powder was composed of 0.68 wt. % Fe, 15.9 wt. % W, and 54.3 wt. % Zr on average. The powder X-ray diffraction pattern (not shown) contained primarily tetragonal zirconium oxide and possibly small amounts of monoclinic tungsten oxide. The average peak height ratio from powder X-ray diffraction of the monoclinic tungsten oxide:monoclinic zirconium oxide was 0.60 after calcination at 750° C. At higher calcination temperatures (>800° C.), the amount of monoclinic tungsten oxide and monoclinic zirconium oxide increased. The resulting surface area was 60 m$^2$/g, and the NH$_3$ uptake was 0.11 mmol/g, each on average.

Example 5: Quadrupled reagent concentrations during co-precipitation. This example was conducted in a similar manner to Example 1, except at a more concentrated scale in both solutions A and B and in the alkaline solution for co-precipitation. Preparation of solution A: In a beaker, 179.4 grams of concentrated NH$_4$OH and 37.3 grams of (NH$_4$)$_6$H$_2$W$_{12}$O$_{40}$·xH$_2$O (66.9% W) (ammonium metatungstate, AMT) were combined with stirring in 250 ml of H$_2$O and heated at 60° C. Preparation of solution B: 345 grams of ZrOCl$_2$·xH$_2$O and 5.3 grams of FeSO$_4$ were dissolved in 250 ml of H$_2$O and heated at 60° C. In a separate vessel, 525 grams of de-ionized water was adjusted to a pH of 9-10 with NH$_4$OH. The alkaline solution was stirred at 40° C. While stirring, solutions A and B were added to the alkaline solution at 10 ml/minute. After the complete addition of the solutions A and B, the slurry was stirred for an hour at 40° C. Upon completion of the co-precipitation, the slurry was transferred to another container (e.g., polypropylene bottle or Teflon bottle), and digested for 72 hours at 100° C. After digestion, the resulting powder was filtered and washed with water. The powder at this point may or may not be washed with NH$_4$NO$_3$. The powder was washed with additional water and dried at 120° C. The powder was then calcined in air in a temperature range from 700° C.-850° C. to prepare the active oxide form of the powder, which was composed of 0.62 wt. % Fe, 16.0 wt. % W, and 54.9 wt. % Zr on average. The powder X-ray diffraction pattern (FIG. 1) contained primarily tetragonal zirconium oxide and possibly small amounts of monoclinic tungsten oxide. The average peak height ratio from the powder X-ray diffraction of the monoclinic tungsten oxide:monoclinic zirconium oxide was 0.90 after calcination at 750° C. At higher calcination temperatures (>800° C.), the amount of monoclinic tungsten oxide and monoclinic zirconium oxide increased. The resulting surface area was 82 m$^2$/g, and the NH$_3$ uptake was 0.14 mmol/g, each on average.

Example 6: Quadrupled reagent concentrations during co-precipitation and digestion in original vessel. This example conducted in the same manner as Example 5, except after stirring for 1 hour at 40° C., the temperature in the vessel was increased to 100° C. and the slurry was digested for 72 hours at 100° C. After digestion, the resulting powder was filtered and washed with water. The powder at this point may or may not be washed with NH$_4$NO$_3$. The powder was washed with additional water and dried at 120° C. The powder was then calcined in air in a temperature ranging from 700° C.-850° C. to prepare the active oxide form of the powder, which was composed of 0.65 wt. % Fe, 16.2 wt. % W, and 54.1 wt. % Zr on average. The powder X-ray diffraction pattern (FIG. 1) contained primarily tetragonal zirconium oxide and possibly small amounts of monoclinic tungsten oxide. The average peak height ratio from powder X-ray diffraction of the monoclinic tungsten oxide:monoclinic zirconium oxide was 1.09 after calcination at 750° C. At higher calcination temperatures (>800° C.), the amount of monoclinic tungsten oxide and monoclinic zirconium oxide increased. The resulting surface area was 87 m$^2$/g, and the NH$_3$ uptake was 0.16 mmol/g, each on average.

Example 7: Quadrupled reagent concentrations during co-precipitation and digestion at 23-25° C. This example conducted in the same manner as Example 5, except digestion was conducted at 23-25° C. After digestion, the resulting powder was filtered and washed with water. The powder at this point may or may not be washed with NH$_4$NO$_3$. The powder was washed with additional water and dried at 120° C. The powder was then calcined in air in a temperature range from 700° C.-850° C. to prepare the active oxide form of the powder, which was composed of 0.71 wt. % Fe, 17.1 wt. % W, and 52.6 wt. % Zr on average. The powder X-ray diffraction pattern (FIG. 1) contained primarily tetragonal zirconium oxide and possibly small amounts of monoclinic tungsten oxide. The average peak height ratio from powder X-ray diffraction of the monoclinic tungsten oxide:monoclinic zirconium oxide was 0.50 after calcination at 750° C. At higher calcination temperatures, (>800° C.), the amount of monoclinic tungsten oxide and monoclinic zirconium oxide increased. The resulting surface area was 62 m$^2$/g, and the NH$_3$ uptake was 0.13 mmol/g, each on average.

Example 8: Quadrupled reagent concentrations during co-precipitation and digestion at 23-25° C. for 1 hr. This example conducted in the same manner as Example 5, except digestion was conducted at 23-25° C. for 1 hour. After digestion, the resulting powder was filtered and washed with water. After digestion, the resulting powder was filtered and washed with water. The powder at this point may or may not be washed with NH$_4$NO$_3$. The powder was washed with additional water and dried at 120° C. The powder was then calcined in air in a temperature range from 700° C.-850° C. to prepare the active oxide form of the powder, which was composed of 0.72 wt. % Fe, 17.4 wt. % W, and 52.3 wt. % Zr on average. The powder X-ray diffraction pattern (FIG. 1) contained primarily tetragonal zirconium oxide and possibly small amounts of monoclinic tungsten oxide. The average peak height ratio from powder X-ray diffraction of the monoclinic tungsten oxide:monoclinic zirconium oxide was 1.38 after calcination at 750° C. At higher calcination temperatures (>800° C.), the amount of monoclinic tungsten oxide and monoclinic zirconium oxide increased. The resulting surface area was 52 m$^2$/g, and the NH$_3$ uptake was 0.10 mmol/g, each on average.

Example 9: Quadrupled reagent concentrations during co-precipitation with further increased W concentration. This example was conducted in a similar manner to Example 5, except with a 25% increase in W concentration. Preparation of solution A: In a beaker, 254.6 grams of concentrated NH$_4$OH and 52.9 grams of (NH$_4$)$_6$H$_2$W$_{12}$O$_{40}$·xH$_2$O (66.9% W) (ammonium metatungstate, AMT) were combined with stirring in 355 ml of H$_2$O, and heated at 60° C. Preparation of solution B: 392 grams of ZrOCl$_2$·xH$_2$O and 6.0 grams of FeSO$_4$ were dissolved in 284 ml of H$_2$O and heated at 60° C. In a separate vessel, 525 grams of deionized water was adjusted to a pH of 9-10 with NH$_4$OH. The alkaline solution was stirred at 40° C. While stirring, solutions A and B were added to the alkaline solution at 10 ml/minute. After the complete addition of solutions A and B, the slurry was stirred for an hour at 40° C. At the completion of the co-precipitation, the slurry was transferred to another container (e.g., polypropylene bottle or Teflon bottle), and digested for 72 hours at 23-25° C. After digestion, the resulting powder was filtered and washed with water. The powder at this point may or may not be washed with NH$_4$NO$_3$. The powder was washed with additional water, and dried at 120° C. The powder was then calcined in air in a temperature range from 700° C.-850° C. to prepare the active oxide form of the powder, which was composed of 0.60 wt. % Fe, 19.2 wt. % W, and 52.0 wt. % Zr on average. The powder X-ray diffraction pattern (not shown) contained primarily tetragonal zirconium oxide and possibly small amounts of monoclinic tungsten oxide. The average peak height ratio from powder X-ray diffraction of the monoclinic tungsten oxide:monoclinic zirconium oxide was 3.86 after calcination at 750° C. At higher calcination temperatures (>800° C.), the amount of monoclinic tungsten oxide and monoclinic zirconium oxide increased. The resulting surface area was 85 m$^2$/g, and the NH$_3$ uptake was 0.16 mmol/g, each on average.

Example 10: Quadrupled reagent concentrations during co-precipitation with further decreased W concentration. This example was conducted in a similar manner to Example 5, except with a 25% decrease in W concentration. Preparation of solution A: In a beaker, 181.8 grams of concentrated NH$_4$OH and 28.0 grams of (NH$_4$)$_6$H$_2$W$_{12}$O$_{40}$·xH$_2$O (66.9% W) (ammonium metatungstate, AMT) were combined with stirring in 248 ml of H$_2$O, and heated to 60° C. Preparation of solution B: 345 grams of ZrOCl$_2$·xH$_2$O and 5.3 grams of FeSO$_4$ were dissolved in 284 ml of H$_2$O and heated at 60° C. In a separate vessel, 525 grams of deionized water was adjusted to a pH of 9-10 with NH$_4$OH. The alkaline solution was stirred at 40° C. While stirring, solutions A and B were added to the alkaline solution at 10 ml/minute. After the complete addition of solutions A and B, the slurry was stirred for an hour at 40° C. At the completion of the co-precipitation, the slurry was transferred to another container (e.g., polypropylene bottle or Teflon bottle), and digested for 72 hours at 23° C.-25° C. After digestion, the resulting powder was filtered and washed with water. The powder at this point may or may not be washed with NH$_4$NO$_3$. The powder was washed with additional water, and dried at 120° C. The powder was then calcined in air in a temperature range from 700° C.-850° C. to prepare the active oxide form of the powder, which was composed of 0.66 wt. % Fe, 13.2 wt. % W, and 56.0 wt. % Zr on average. The powder X-ray diffraction pattern (not shown) contained primarily tetragonal zirconium oxide and possibly small amounts of monoclinic tungsten oxide. The average peak height ratio from powder X-ray diffraction of the monoclinic tungsten oxide:monoclinic zirconium oxide was 0.31 after calcination at 750° C. At higher calcination temperatures, (>800° C.), the amount of monoclinic tungsten oxide and monoclinic zirconium oxide increased. The resulting surface area was 86 m$^2$/g, and the NH$_3$ uptake was 0.17 mmol/g, each on average.

Example 11: Quadrupled reagent concentrations during co-precipitation with doubled Fe concentration. This example was conducted in the same manner as Example 5, except the amount of FeSO$_4$ was doubled (10.5 grams). After digestion, the resulting powder was filtered and washed with water. The powder at this point may or may not be washed with NH$_4$NO$_3$. The powder was washed with additional water and dried at 120° C. The powder was then calcined in air in a temperature range from 700° C.-850° C. to prepare the active oxide form of the powder, which was composed of approximately 1.25 wt. % Fe, 16.0 wt. % W, and 54.0 wt. % Zr on average. The powder X-ray diffraction pattern (not shown) contained primarily tetragonal zirconium oxide and possibly small amounts of monoclinic tungsten oxide. The average peak height ratio from powder X-ray diffraction of the monoclinic tungsten oxide:monoclinic zirconium oxide was 1.74 after calcination at 750° C. At higher calcination temperatures (>800° C.), the amount of monoclinic tungsten oxide and monoclinic zirconium oxide increased. The resulting surface area was 80 m$^2$/g, and the NH$_3$ uptake was 0.16 mmol/g, each on average.

Example 12: Quadrupled reagent concentrations during co-precipitation with 5-fold less Fe concentration. This example was conducted in the same manner as Example 5, except the amount of FeSO$_4$ was decreased 5-fold (1.1 grams). After digestion, the resulting powder was filtered and washed with water. The powder at this point may or may not be washed with NH$_4$NO$_3$. The powder was washed with additional water, and dried at 120° C. The powder was then calcined in air in a temperature range from 700° C.-850° C. to prepare the active oxide form of the powder, which was composed of 0.15 wt. % Fe, 16.9 wt. % W, and 54.1 wt. % Zr on average. The powder X-ray diffraction pattern (not shown) contained primarily tetragonal zirconium oxide and possibly small amounts of monoclinic tungsten oxide. The average peak height ratio from powder X-ray diffraction of the monoclinic tungsten oxide:monoclinic zirconium oxide was 1.08 after calcination at 750° C. At higher calcination temperatures (>800° C.), the amount of monoclinic tungsten oxide and monoclinic zirconium oxide increased. The resulting surface area was 86 m$^2$/g, and the NH$_3$ uptake was 0.16 mmol/g, each on average.

Example 13: Substitution of Cu for Fe in initial reagent conditions. This example was conducted in the same manner as Example 1, except substituting 1.7 grams of CuSO$_4$ for FeSO$_4$. After digestion, the resulting powder was filtered and washed with water. The powder at this point may or may not be washed with NH$_4$NO$_3$. The powder was washed with additional water and dried at 120° C. The powder was then calcined in air in a temperature range from 700° C.-850° C. to prepare the active oxide form of the powder, which was composed of 0.5 wt. % Cu, 15 wt. % W, and 54 wt. % Zr on average. The powder X-ray diffraction pattern (not shown) contained primarily tetragonal zirconium oxide and possibly small amounts of monoclinic tungsten oxide. At higher calcination temperatures (>800° C.), the amount of monoclinic tungsten oxide and monoclinic zirconium oxide increased. The resulting surface area was 91 m$^2$/g, and the NH$_3$ uptake was 0.17 mmol/g, each on average.

Example 14: Substitution of Mn for Fe in initial reagent conditions. This example conducted in the same manner as Example 1, except substituting 1.7 grams of MnSO$_4$ for FeSO$_4$. After digestion, the resulting powder was filtered and washed with water. The powder at this point may or may not be washed with NH$_4$NO$_3$. The powder was washed with additional water and dried at 120° C. The powder was then calcined in air in a temperature range from 700° C.-850° C.

to prepare the active oxide form of the powder, which was composed of 0.5 wt. % Mn, 15 wt. % W, and 54 wt. % Zr on average. The powder X-ray diffraction pattern (not shown) contained primarily tetragonal zirconium oxide and possibly small amounts of monoclinic tungsten oxide. At higher calcination temperatures (>800° C.), the amount of monoclinic tungsten oxide and monoclinic zirconium oxide increased. The resulting surface area was 88 m$^2$/g, and the NH$_3$ uptake was 0.18 mmol/g, each on average.

Example 15: Substitution of Ce for Fe in initial reagent conditions. This example conducted in the same manner as Example 1, except substituting 2.0 grams of Ce$_2$(SO$_4$)$_3$ hydrate for FeSO$_4$. After digestion, the resulting powder was filtered and washed with water. The powder at this point may or may not be washed with NH$_4$NO$_3$. The powder was washed with additional water and dried at 120° C. The powder was then calcined in air in a temperature range from 700° C.-850° C. to prepare the active oxide form of the powder, which was composed of 0.5 wt. % Ce, 15 wt. % W and 54 wt. % Zr on average. The powder X-ray diffraction pattern (not shown) contained primarily tetragonal zirconium oxide and possibly small amounts of monoclinic tungsten oxide. At higher calcination temperatures (>800° C.), the amount of monoclinic tungsten oxide and monoclinic zirconium oxide increased. The resulting surface area was 93 m$^2$/g, and the NH$_3$ uptake was 0.18 mmol/g, each on average.

Example 16: Quadrupled reagents concentrations during co-precipitation with no Fe. This example was conducted in a similar manner to Example 5, except no FeSO$_4$ was included in the reaction mixture in solution B. After digestion, the resulting powder was filtered and washed with water. The powder at this point may or may not be washed with NH$_4$NO$_3$. The powder was washed with additional water, and dried at 120° C. The powder was then calcined in air in a temperature range from 700° C.-850° C. to prepare the active oxide form of the powder, which was composed of 0.02 wt. % Fe, 15 wt. % W, and 55 wt. % Zr on average. The powder X-ray diffraction pattern (not shown) contained primarily tetragonal zirconium oxide and possibly small amounts of monoclinic tungsten oxide. At higher calcination temperatures (>800° C.), the amount of monoclinic tungsten oxide and monoclinic zirconium oxide increased. The resulting surface area was 100 m$^2$/g, and the NH$_3$ uptake was 0.20 mmol/g, each on average.

Example 17: General extrusion conditions. Self-bound extrusion of powder samples was carried out on a 1" DIAMOND AMERICA extruder using 100 g of powder mulled for 5 minutes in a LANCASTER muller. Following an initial mulling period, 10 g of CAPLUBE® ethoxylated castor oil, was added to the mulled powder, and mulling was conducted for an additional 5 minutes. A sufficient amount of water was then added to form a paste for extrusion of 1/16" quadrulobes. After extrusion, the extrudates were dried at 120° C. for several hours. The extrudates may or may not be washed with NH$_4$NO$_3$. After drying, the extrudates were calcined at 1000° F. (537.7° C.) for 4 hours to prepare the final extrudates. Typical crush strengths for this type of extrudate were >50 lbs/in.

Example 18: Pt loading using H$_2$PtCl$_6$ to a targeted metal content of 0.5 wt. %. Water uptake was measured to determine the amount of water needed for incipient wetness impregnation of metal salt onto the extrudates. Taking 95%-98% of the water uptake, the amount of stock metal salt solution for dilution was subtracted to determine the amount of water required to form a diluted metal salt solution for impregnation. 50 g of extrudate was impregnated with 6.5 g of 3.8% Pt solution of H$_2$PtCl$_6$, diluted with 3.3 g of water. The amount of Pt solution was chosen to target a 0.5 wt. % Pt loading upon the extrudates. The solution was sprayed onto the dried extrudates. The extrudates were then dried at 120° C. The extrudates were then calcined in air at 300° C. for 3 hours to produce the oxide form of the Pt salt. The Pt dispersion upon the extrudates ranged between 30% and 45%, as measured via CO chemisorption. The extrudates were reduced under hydrogen at 180° C.-220° C. for 2 to 3 hours to prepare the active form of the catalyst.

Example 19: Pt loading using (NH$_3$)$_4$Pt(NO$_3$)$_2$ to a targeted metal content of 0.5 wt. %. This example was performed in a similar manner to Example 18, except 7.9 g of 3.2% (NH$_3$)$_4$Pt(NO$_3$)$_2$ was diluted with 2.0 g of water and used for metal impregnation. The metal dispersion upon the extrudates ranged between 25% and 40%, as measured by CO chemisorption. The extrudates were reduced under hydrogen at 180° C.-220° C. for 2 to 3 hours to prepare the active form of the catalyst.

Table 1 summarizes various properties of the samples produced in Examples 1-12. Surface area was determined by N$_2$ BET adsorption/desorption isotherms. NH$_3$ uptake was measured by temperature programmed adsorption/desorption, and collidine uptake was measured gravimetrically. X-ray powder diffraction peaks were determined using Cu Kα radiation. The following approximate 2θ peak positions are characteristic: m-WO$_3$=24.4°, m-ZrO$_2$=28.4°, and tetragonal ZrO$_2$ (t-ZrO$_2$)=30.2°.

TABLE 1

| Example | Average XRD Peak Height Ratio (m-WO$_3$/m-ZrO$_2$) | Average Total Surface Area (m$^2$/g) | Average Ammonia Uptake (mmol/g) |
| --- | --- | --- | --- |
| 1 | 0.55 | 89 | 0.16 |
| 2 | 0.53 | 96 | 0.17 |
| 3 | 0.44 | 93 | 0.19 |
| 4 | 0.60 | 60 | 0.11 |
| 5 | 0.90 | 82 | 0.14 |
| 6 | 1.09 | 87 | 0.16 |
| 7 | 0.50 | 62 | 0.13 |
| 8 | 1.38 | 52 | 0.10 |
| 9 | 3.86 | 85 | 0.16 |
| 10 | 0.31 | 86 | 0.17 |
| 11 | 1.74 | 80 | 0.16 |
| 12 | 1.08 | 86 | 0.16 |

Table 2 summarizes the compositional profiles, including the W surface density, of the samples produced in Examples 1-12. The tungsten (W) surface density was calculated from (a) the measured W content (wt. %) obtained by X-ray fluorescence and (b) the measured surface area obtained by N$_2$ BET.

TABLE 2

| Example | Average wt. % Zr | Average wt. % W | Average wt. % Fe | Average W Surface Density (W atoms/nm$^2$) |
| --- | --- | --- | --- | --- |
| 1 | 54.0 | 15.4 | 0.61 | 5.8 |
| 2 | 54.1 | 16.4 | 0.65 | 5.6 |
| 3 | 64.1 | 8.9 | 0.51 | 3.1 |
| 4 | 54.3 | 15.9 | 0.68 | 8.7 |
| 5 | 54.9 | 16.0 | 0.62 | 6.6 |
| 6 | 54.1 | 16.2 | 0.65 | 6.9 |
| 7 | 52.6 | 17.1 | 0.71 | 9.1 |
| 8 | 52.3 | 17.4 | 0.72 | 11.1 |
| 9 | 52.0 | 19.2 | 0.60 | 7.4 |
| 10 | 56.0 | 13.2 | 0.66 | 5.1 |

TABLE 2-continued

| Example | Average wt. % Zr | Average wt. % W | Average wt. % Fe | Average W Surface Density (W atoms/nm$^2$) |
|---|---|---|---|---|
| 11 | 54.0 | 16.0 | 1.25 | 6.5 |
| 12 | 54.1 | 16.9 | 0.15 | 6.4 |

FIG. 1 is a graph showing powder XRD profiles of the samples produced in Examples 5-8 and their corresponding surface areas. The powder XRD patterns showed the amount of monoclinic tungsten oxide and monoclinic zirconium oxide formed under different synthesis conditions.

Figure 2A:
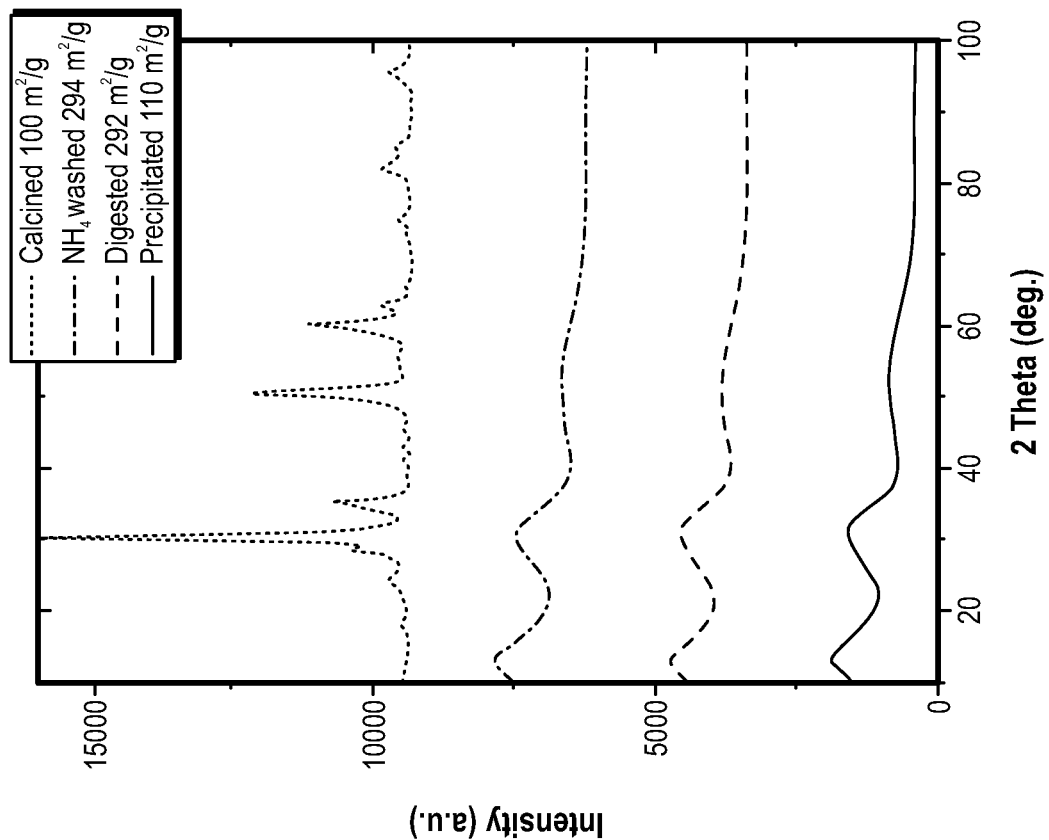
FIGS. 2A and 2B are graphs showing powder XRD profiles of the samples produced in Examples 1 and 5, respectively, at various stages of processing and the corresponding surface areas.
Figure 2B:
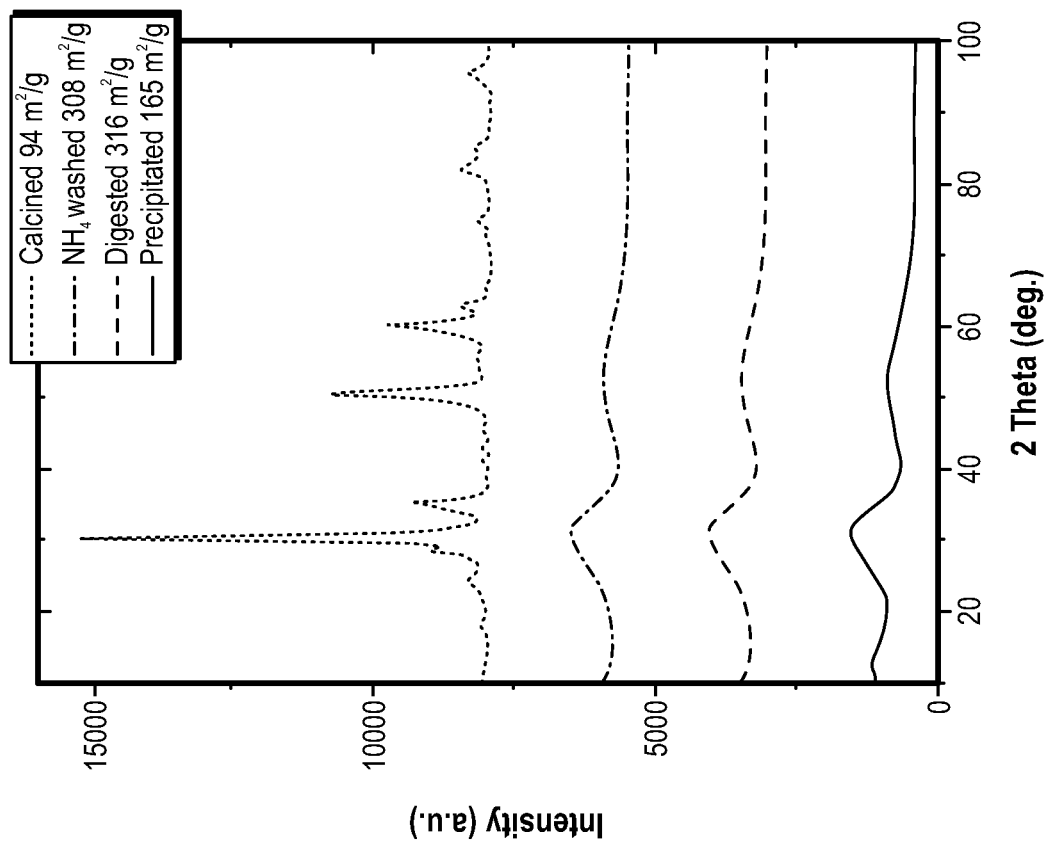

FIGS. 2A and 2B are graphs showing powder XRD profiles of the samples produced in Examples 1 and 5, respectively, at various stages of processing and the corresponding surface areas. The powder XRD patterns of both samples showed broad diffraction peaks in the uncalcined materials (hydroxides), which may be related to a layered precursor prior to calcination. The layered precursors had a significantly higher surface area than did the calcined products. Upon calcination at elevated temperatures, small tungsten oxides clusters and tetragonal zirconium oxide were formed.

Figure 3:
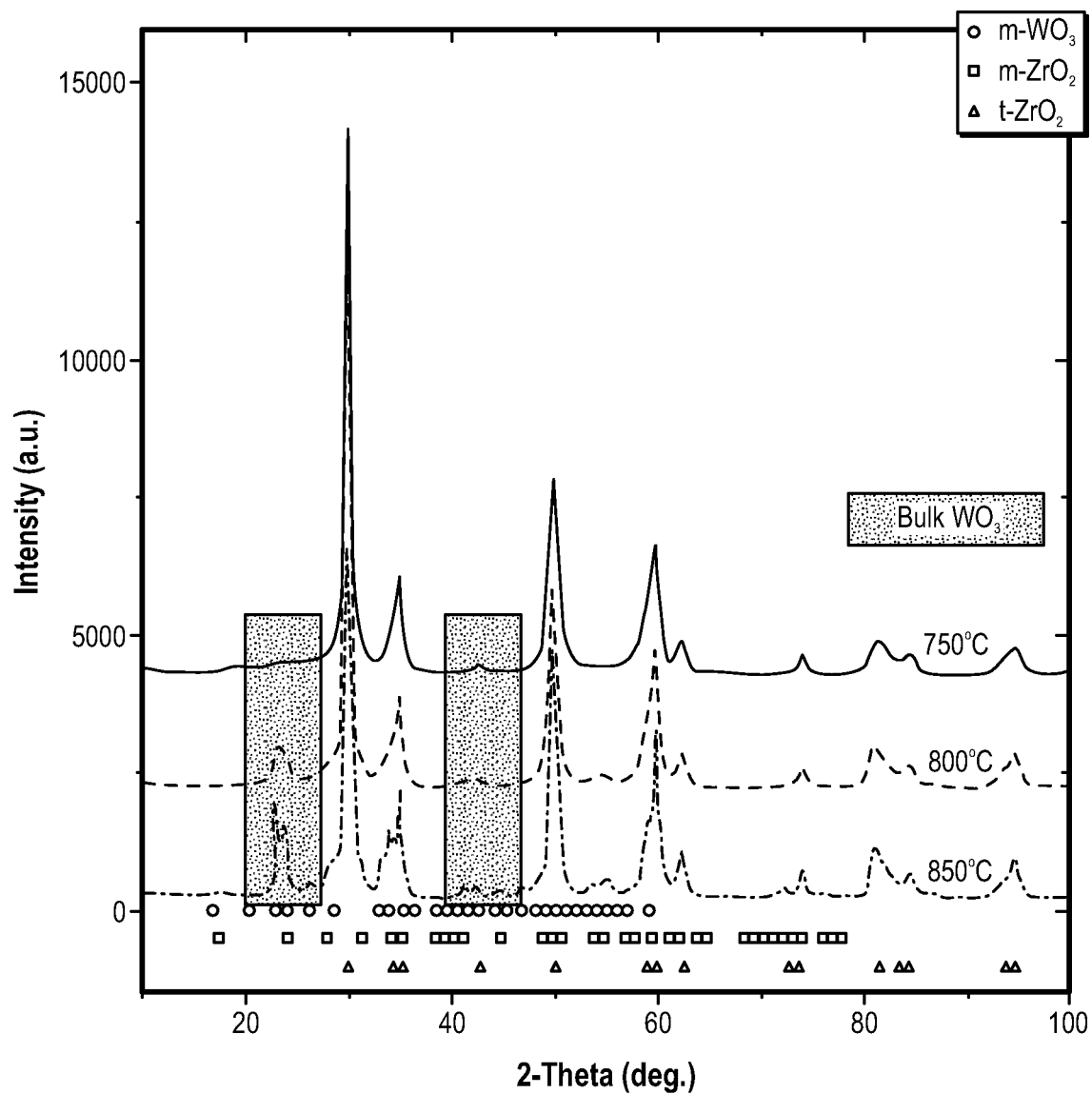
FIG. 3 is a graph showing the powder XRD profile of the mixed metal oxide of Example 5 calcined at three different temperatures.

FIG. 3 is a graph showing the powder XRD profile of the mixed metal oxide of Example 5 calcined at three different temperatures. As the temperature increased beyond a threshold value, monoclinic tungsten oxide species and monoclinic zirconium oxide were formed with a subsequent decrease in the surface area, all decreasing the activity of the catalyst.

Figure 4:
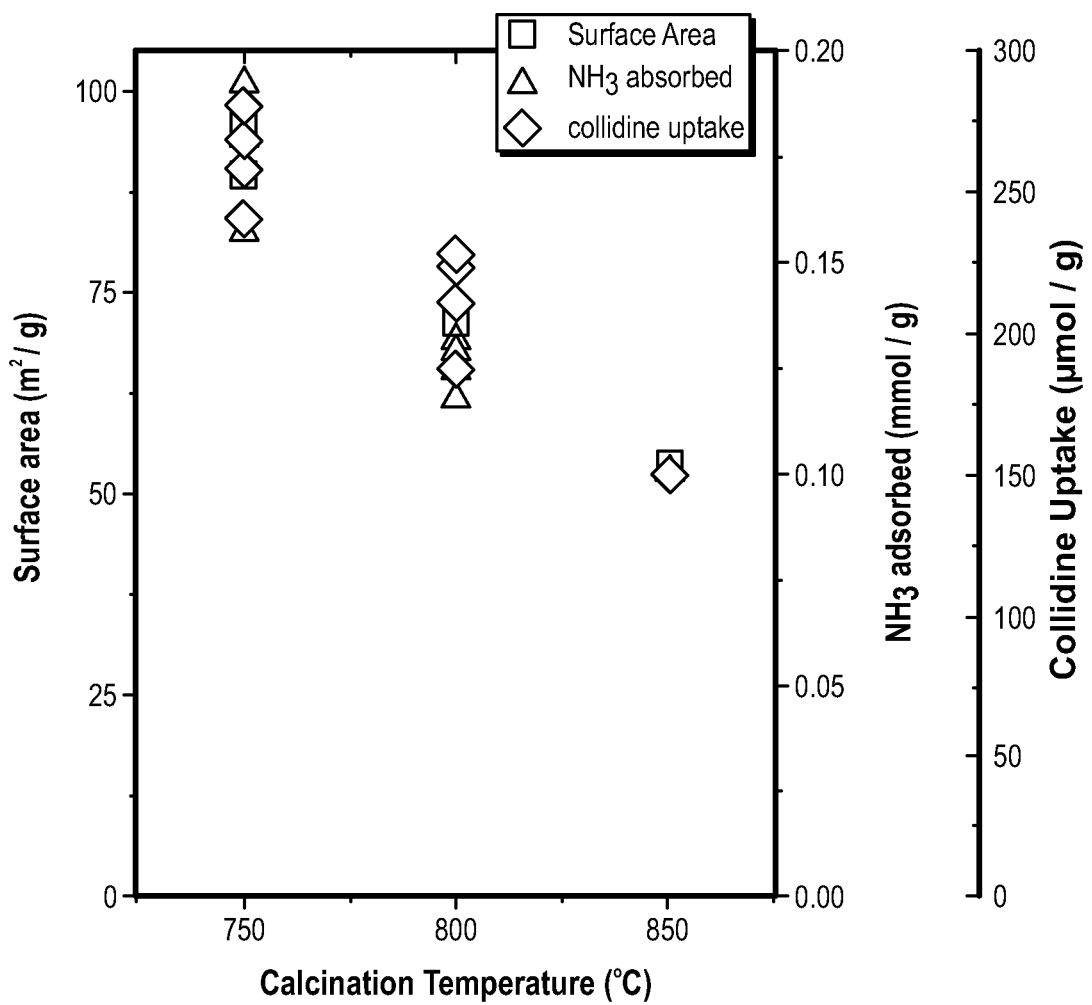
FIG. 4 is a graph showing the variance of surface acidity as a function of calcination temperature for the mixed metal oxide of Example 5.

Table 3 illustrates the effects of the calcination temperature on various properties of the mixed metal oxide produced in Example 5. Ammonia and collidine uptake values (representative of the surface acidity) were measured prior to formation of the active catalyst. FIG. 4 is a graph showing the variance of surface acidity as a function of calcination temperature for the mixed metal oxide produced in Example 5.

TABLE 3

| Entry | Calcination Temperature (° C.) | Powder XRD Peak Height Ratio (m-WO$_3$/m-ZrO$_2$) | Total Surface Area (m$^2$/g) | Ammonia Uptake (mmol/g) |
|---|---|---|---|---|
| 1 | 750 | 0.50 | 98 | 0.19 |
| 2 | 800 | 0.67 | 70 | 0.13 |
| 3 | 850 | 2.07 | 54 | 0.10 |

| Entry | Wt. % Zr | wt. % W | Wt. % Fe | W Surface Density (W atoms/nm$^2$) |
|---|---|---|---|---|
| 1 | 54.2 | 16.3 | 0.66 | 5.5 |
| 2 | 54.2 | 16.3 | 0.66 | 7.7 |
| 3 | 53.4 | 16.9 | 0.67 | 10.3 |

Performance testing of some of the samples is provided below. The data were either collected on high throughput equipment (16-channel flow unit developed by the GmbH high throughput experimentation (HTE) company) or a micro-unit. All examples were extruded as self-bound materials and impregnated with chloroplatinic acid, targeting 0.5 wt. % Pt, as described in Examples 17 and 18, unless designated differently.

Figure 5:
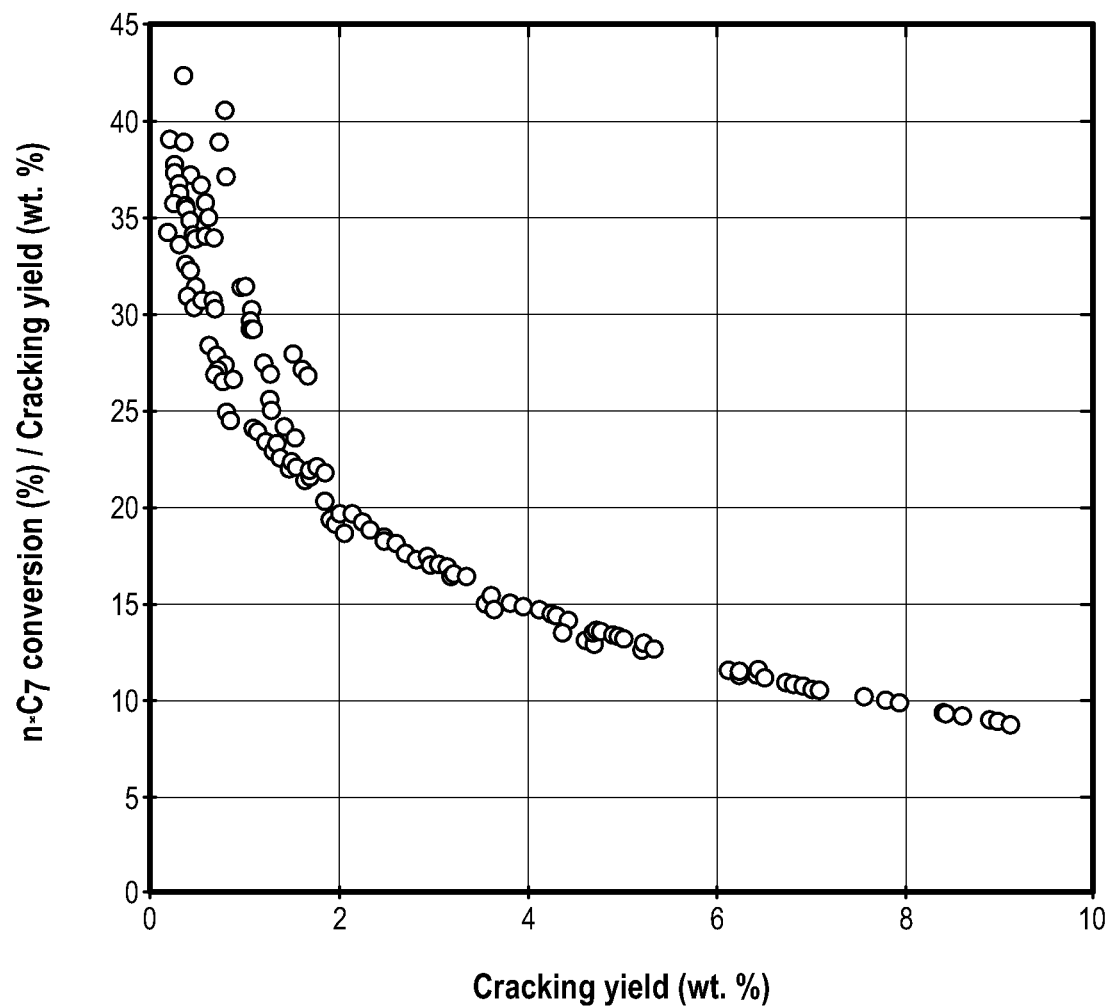
FIG. 5 is a graph of the ratio of n-heptane conversion: cracking yield as a function of cracking yield for the mixed metal oxide of Example 5 at a temperature of 160° C., 200 psig, and a $H_2$:n-heptane ratio of 2:1.

FIG. 5 is a graph of the ratio of n-heptane conversion:cracking yield as a function of cracking yield for the mixed metal oxide of Example 5 at a temperature of 160° C., 200 psig, and a H$_2$:n-heptane ratio of 2:1. Under various LHSV values, cracking yields up to about 9% were observed. As shown, the ratio of n-heptane conversion:cracking yield markedly increased at low cracking yields. At about 5% cracking yield, the ratio was about 13.

Tables 4-8 summarize isomerization data obtained from various samples prepared in the examples described above and reacted under the conditions specified below.

Table 4 summarizes reaction data taken at 170° C., 257 psig, 2 LHSV, and a H$_2$:hydrocarbon ratio of 2:1 in the presence of various catalyst samples. At a LHSV of 2 hr$^{-1}$, 170° C. and 250 psig, greater than 80% n-heptane conversion was realized. Catalyst activation was carried out as follows: The catalysts were heated at 300° C. under 100 sccm N$_2$ for 1 hour and then heated at 220° C. under 100 sccm H$_2$ at 350 psig for 3 hrs. RON was determined as specified in Ghosh, et al., Ind. Eng. Chem. Res., 2006, pp. 337-345, 45.

TABLE 4

| Sample Description | n-Heptane Conversion | Cracking Yield (wt. %) | RON |
|---|---|---|---|
| 750° C. calcined (Example 5) | 50 | 3 | 17 |
| 800° C. calcined (Example 5) | 88 | 18 | 53 |
| 850° C. calcined (Example 5) | 60 | 5 | 23 |
| 750° C. calcined, no Fe (Example 16) | 76 | 10 | 36 |
| 750° C. calcined, high WO$_3$ crystals (XRD peak height ratio >> 3) | 54 | 4 | 20 |
| 750° C. calcined, low concentration (Example 1) | 50 | 3 | 17 |
| 800° C. calcined, Pt nitrate (Example 19) | 60 | 3 | 23 |

Table 5 summarizes reaction data taken at 160° C., 207 psig, 4 LHSV, and a H$_2$:hydrocarbon ratio of 2:1. Catalysts were activated in the same manner as those in Table 4.

TABLE 5

| Sample Description | n-Heptane Conversion | Cracking Yield (wt. %) | RON |
|---|---|---|---|
| 750° C. calcined (Example 5) | 34 | 2 | 9 |
| 800° C. calcined (Example 5) | 57 | 4 | 20 |
| 850° C. calcined (Example 5) | 21 | 1 | 5 |
| 750° C. calcined, no Fe (Example 16) | 37 | 2 | 11 |
| 750° C. calcined, high WO$_3$ crystals (XRD peak height ratio >> 3) | 15 | 1 | 4 |
| 750° C. calcined, low concentration (Example 1) | 15 | 1 | 4 |
| 800° C. calcined, Pt nitrate (Example 19) | 21 | 1 | 5 |

Table 6 illustrates reaction data taken at 160° C., 207 psig, 2 LHSV, and a H$_2$:hydrocarbon ratio of 2:1. Greater than 60% conversion of n-heptane was realized under these conditions. Catalysts were activated in the same manner as those in Table 4.

TABLE 6

| Sample Description | n-Heptane Conversion | Cracking Yield (wt. %) | RON |
|---|---|---|---|
| 750° C. calcined (Example 5) | 61 | 4 | 23 |
| 800° C. calcined (Example 5) | 78 | 8 | 38 |
| 850° C. calcined (Example 5) | 39 | 2 | 11 |
| 750° C. calcined, no Fe (Example 16) | 60 | 5 | 22 |
| 750° C. calcined, high WO$_3$ crystals (XRD peak height ratio >> 3) | 33 | 1 | 9 |
| 750° C. calcined, low concentration (Example 1) | 31 | 1 | 8 |
| 800° C. calcined, Pt nitrate (Example 19) | 43 | 2 | 13 |

Table 7 shows reaction data for individual feeds of n-pentane, n-hexane, and n-heptane isomerized in the presence of samples prepared under various process conditions. Reaction data was taken at 170° C., 188 psig, 3 WHSV, and a H$_2$:hydrocarbon ratio of 2:1. Under these conditions, >25% of the n-pentane, >55% of the n-hexane, and >90% of the n-heptane in the feed mixture underwent conversion. Catalyst activation was carried out as follows: heat at 300° C. under 100 sccm N$_2$ for 1 hour and then heat under 100 sccm H$_2$ at 350 psig at 220° C. for 24 hours.

TABLE 7

| Sample Description | n-Pentane conversion (%) | n-Hexane conversion (%) | n-Heptane conversion (%) |
|---|---|---|---|
| Standard (Example 5) | 7 | 42 | 85 |
| 75% W (Example 10) | 4 | 25 | 64 |
| 125% W (Example 9) | 6 | 36 | 85 |
| Open autoclave (process variation) | 4 | 25 | 74 |
| Closed autoclave (process variation) | 5 | 31 | 82 |
| Extrude then calcine (process variation) | 4 | 24 | 74 |
| No NH$_4^+$ wash before calcine (process variation) | 5 | 32 | 83 |
| No NH$_4^+$ washes (process variation) | 3 | 17 | 61 |

Table 8 shows reaction data at various temperatures for individual feeds of n-pentane and n-hexane for a catalyst (Example 5) calcined at 750° C. and impregnated with noble metal. Reaction data was collected 350 psig, 2 LHSV, and a H$_2$:hydrocarbon ratio of 2:1. Catalyst activation was carried out as follows: heat at 300° C. under 100 sccm N$_2$ for 1 hour and then heat under 100 sccm H$_2$ at 350 psig at 180° C. for 3 hours (microunit).

TABLE 8

| Temperature (° C.) | n-Pentane Conversion | RON after Pentane Isomerization | n-Hexane Conversion | RON after Hexane Isomerization |
|---|---|---|---|---|
| 180 | 6 | 64 | 14 | 33 |
| 190 | 13 | 66 | 43 | 48 |
| 200 | 26 | 70 | 68 | 63 |
| 210 | 44 | 75 | 80 | 70 |
| 220 | 60 | 80 | 84 | 73 |
| 230 | 69 | 83 | 85 | 73 |

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

One or more illustrative incarnations incorporating one or more invention elements are presented herein. Not all features of a physical implementation are described or shown in this application for the sake of clarity. It is understood that in the development of a physical embodiment incorporating one or more elements of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed, including the lower limit and upper limit. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

What is claimed is:

1. A composition comprising:
   a mixed metal oxide that is at least partially crystalline and comprises tungsten, zirconium, and a variable oxidation state metal;
   wherein the variable oxidation state metal comprises a metal selected from the group consisting of Fe, Mn, Co, Cu, Ce, Ni, and any combination thereof;
   wherein the mixed metal oxide comprises about 5 wt. % to about 25 wt. % tungsten, about 40 wt. % to about 70 wt. % zirconium, and about 0.01 wt. % to about 2 wt. % variable oxidation state metal, each based on a total mass of the mixed metal oxide; and
   wherein the mixed metal oxide has a total surface area of between 50 $m^2/g$ and 150 $m^2/g$ as measured according to ISO 9277, and at least one of the following:
   an ammonia uptake of about 0.05 to about 0.3 mmol/g as measured by temperature programmed adsorption/desorption, or
   a collidine uptake of about 100 μmol/g or greater as measured gravimetrically.

2. The composition of claim 1, wherein the mixed metal oxide is impregnated with a noble metal, the noble metal being present at about 0.01 wt. % to about 2 wt. % based on total mass of the mixed metal oxide plus noble metal.

3. The composition of claim 2, wherein the noble metal comprises at least one noble metal selected from the group consisting of Pt, Pd, Rh, and any combination thereof.

4. The composition of claim 2, wherein the mixed metal oxide, when activated, is effective to isomerize n-heptane at a conversion:cracking yield ratio of about 10 or greater at about 10% or less cracking yield.

5. The composition of claim 1, wherein the mixed metal oxide has a total surface area ranging from about 60 $m^2/g$ to about 130 $m^2/g$.

6. The composition of claim 1, wherein the mixed metal oxide has a tungsten surface density, measured as W atoms/$nm^2$, ranging from about 2 to about 20.

7. The composition of claim 1, wherein the mixed metal oxide has an X-ray powder diffraction peak height ratio ranging from 0 to about 5 for monoclinic tungsten oxide (m-$WO_3$) relative to monoclinic zirconium oxide (m-$ZrO_2$).

8. The composition of claim 1, wherein the mixed metal oxide comprises about 9 wt. % to about 20 wt. % tungsten, about 40 wt. % to 70 wt. % Zr, and about 0.01 wt. % to 2 wt. % variable oxidation state metal, each based on total mass of the mixed metal oxide.

9. The composition of claim 8, wherein the mixed metal oxide comprises about 0.5 wt. % to 0.7 wt. % variable oxidation state metal, based on total mass of the mixed metal oxide.

10. The composition of claim 8, wherein the variable oxidation state metal is selected from the group consisting of Fe, Mn, Cu, Ce, and any combination thereof.

11. The composition of claim 1, wherein the variable oxidation state metal comprises Fe.

12. The composition of claim 1, further comprising:
    a binder combined with the mixed metal oxide.

13. A method comprising:
    combining a zirconium source, a tungsten source, and a variable oxidation state metal source in a reaction mixture under alkaline conditions having a pH of about 7.5 or greater;
    wherein the variable oxidation state metal comprises a metal selected from the group consisting of Fe, Mn, Co, Cu, Ce, Ni, and any combination thereof;
    obtaining under the alkaline conditions a slurry comprising a co-precipitate reaction product formed from the zirconium source, the tungsten source, and the variable oxidation state metal source;
    digesting the slurry and forming an amorphous digestion product from the co-precipitate reaction product; and
    calcining the amorphous digestion product in air at a temperature ranging from about 700° C. to about 900° C. to obtain a mixed metal oxide that is at least partially crystalline and comprises about 5 wt. % to about 25 wt. % tungsten, about 40 wt. % to about 70 wt. % zirconium, and about 0.01 wt. % to about 2 wt. % variable oxidation state metal, each based on a total mass of the mixed metal oxide;
    wherein the mixed metal oxide has a total surface area of about 50 $m^2/g$ or greater as measured according to ISO 9277, and at least one of the following:
    an ammonia uptake of about 0.05 to about 0.3 mmol/g as measured by temperature programmed adsorption/desorption, or
    a collidine uptake of about 100 μmol/g or greater as measured gravimetrically.

14. The method of claim 13, wherein the reaction mixture is formed by combining a first solution comprising the tungsten source, and a second solution comprising the zirconium source and the variable oxidation state metal source in an alkaline solution having a pH of about 9 to about 10.

15. The method of claim 13, wherein the mixed metal oxide is impregnated with a noble metal, the noble metal being present at about 0.01 wt. % to about 2 wt. %, based on total mass of the mixed metal oxide plus noble metal.

16. The method of claim 13, further comprising:
    after calcining, introducing a noble metal precursor to the mixed metal oxide by incipient wetness impregnation, vacuum infiltration impregnation, or any combination thereof.

17. The method of claim 15, wherein the noble metal comprises at least one noble metal selected from the group consisting of Pt, Pd, Rh, and any combination thereof.

18. The method of claim 16, wherein the noble metal precursor comprises a water-soluble metal complex selected from the group consisting of (NH$_3$)$_4$Pt(NO$_3$)$_2$, (NH$_3$)$_4$Pt(OH)$_2$, (NH$_3$)$_4$PtCl$_2$, H$_2$PtCl$_6$, and any combination thereof.

19. The method of claim 13, wherein the mixed metal oxide comprises about 9 wt. % to about 20 wt. % tungsten, about 40 wt. % to 70 wt. % Zr, and about 0.01 wt. % to 2 wt. % variable oxidation state metal, each based on total mass of the mixed metal oxide.

20. The method of claim 19, wherein the mixed metal oxide comprises about 0.5 wt. % to 0.7 wt. % variable oxidation state metal, based on total mass of the mixed metal oxide.

21. The method of claim 13, wherein the variable oxidation state metal is selected from the group consisting of Fe, Mn, Cu, Ce, and any combination thereof.

22. The method of claim 13, wherein the variable oxidation state metal comprises Fe.

23. The method of claim 13, further comprising:
forming an extrudate from the mixed metal oxide.

24. The method of claim 23, where the mixed metal oxide is co-extruded with a binder to form the extrudate.

25. The method of claim 24, wherein the binder comprises at least one substance selected from the group consisting of a W/Zr oxide, a W/Zr hydroxide, a W oxide, a W hydroxide, a Zr oxide, a Zr hydroxide, an Fe oxide, an Fe hydroxide, a Ti oxide, a Ti hydroxide, silica, silica alumina, a titania silica, an aluminum oxide, an aluminum hydroxide, and any combination thereof.

26. The method of claim 13, wherein the mixed metal oxide has an X-ray powder diffraction peak height ratio ranging from 0 to about 5 for monoclinic tungsten oxide (m-WO$_3$) relative to monoclinic zirconium oxide (m-ZrO$_2$).

27. A method comprising:
heating a mixed metal oxide under hydrogen to form an activated catalyst, the mixed metal oxide being at least partially crystalline and comprising about 5 wt. % to about 25 wt. % tungsten, about 40 wt. % to about 70 wt. % zirconium, and about 0.01 wt. % to about 2 wt. % variable oxidation state metal, wherein the mixed metal oxide is further impregnated with about 0.01 wt. % to about 2 wt. % noble metal, each based on a total mass of the mixed metal oxide plus noble metal;
wherein the mixed metal oxide has a total surface area of between 50 m$^2$/g and 150 m$^2$/g as measured according to ISO 9277, and at least one of the following:
an ammonia uptake of about 0.05 to about 0.3 mmol/g as measured by temperature programmed adsorption/desorption, or
a collidine uptake of about 100 μmol/g or greater as measured gravimetrically;
contacting the activated catalyst with a hydrocarbon feedstock under isomerization reaction conditions, the hydrocarbon feedstock comprising at least one C$_{7+}$ normal alkane; and
forming one or more branched alkanes from the at least one C$_{7+}$ normal alkane.

28. The method of claim 27, wherein the activated catalyst is effective to isomerize n-heptane at a conversion:cracking yield ratio of about 10 or greater at about 10% or less cracking yield.

29. The method of claim 27, wherein the isomerization reaction conditions comprise one or more of the following:
a temperature ranging from about 150° C. to about 210° C.;
a ratio of hydrogen to hydrocarbon feedstock ranging from about 1:1 to about 3:1;
a pressure ranging from about 150 psig to about 350 psig; and
a liquid hourly space velocity ranging from about 0.5 h$^{-1}$ to about 6 h$^{-1}$.

30. The method of claim 27, wherein the mixed metal oxide has a total surface area ranging from about 60 m$^2$/g to about 130 m$^2$/g, and/or a tungsten surface density, measured as W atoms/nm$^2$, ranging from about 2 to about 20.

31. The method of claim 27, wherein the mixed metal oxide has an X-ray powder diffraction peak height ratio ranging from 0 to about 5 for monoclinic tungsten oxide (m-WO$_3$) relative to monoclinic zirconium oxide (m-ZrO$_2$).

* * * * *